(12) United States Patent
Brünjes et al.

(10) Patent No.: US 8,309,557 B2
(45) Date of Patent: Nov. 13, 2012

(54) PYRIMIDIN-4-YLPROPANEDINITRILE DERIVATIVES, PROCESSES FOR THEIR PREPARATION AND THEIR USE AS HERBICIDES AND PLANT GROWTH REGULATORS

(75) Inventors: Marco Brünjes, Hofheim (DE); Hansjörg Dietrich, Liederbach am Taunus (DE); Hartmut Ahrens, Egelsbach (DE); Michael Gerhard Hoffmann, Flörsheim (DE); Jan Dittgen, Frankfurt (DE); Dieter Feucht, Eschborn (DE); Christopher Hugh Rosinger, Hofheim (DE); Isolde Häuser-Hahn, Leverkusen (DE)

(73) Assignee: Bayer Intellectual Property GmbH, Monheim (DE)

( * ) Notice: Subject to any disclaimer, the term of this patent is extended or adjusted under 35 U.S.C. 154(b) by 53 days.

(21) Appl. No.: 12/724,706

(22) Filed: Mar. 16, 2010

(65) Prior Publication Data

US 2010/0240536 A1    Sep. 23, 2010

(30) Foreign Application Priority Data

Mar. 21, 2009  (EP) .................................... 09004084

(51) Int. Cl.
*A01N 43/54* (2006.01)
*C07D 239/42* (2006.01)
*C07D 401/04* (2006.01)
(52) U.S. Cl. ..................................................... 514/256
(58) Field of Classification Search ................... 504/239; 544/326, 334
See application file for complete search history.

(56) References Cited

U.S. PATENT DOCUMENTS 4,014,677 A    3/1977    Fischer

FOREIGN PATENT DOCUMENTS

| DE | 25 20 381 | 11/1975 |
| EP | 0 136 976 A2 | 4/1985 |
| WO | 2005/063721 A1 | 7/2005 |
| WO | 2007/082076 A1 | 7/2007 |

OTHER PUBLICATIONS

A. Fadda et al., Monatshefte fuer Chemie, 130, 1487-1492 (1999).*
Lamberth, "Pyrimidine Chemistry in Crop Protection"; Heterocycles, vol. 68, No. 3, 2006.
International Search Report based on PCT/EP2010/001600 dated Sep. 3, 2010.

* cited by examiner

*Primary Examiner* — James O Wilson
*Assistant Examiner* — Alexander R Pagano
(74) *Attorney, Agent, or Firm* — Baker Donelson Bearman, Caldwell & Berkowitz, PC

(57) ABSTRACT

The invention relates to compounds of the formula (I) and N-oxides, tautomers and agrochemically compatible salts thereof

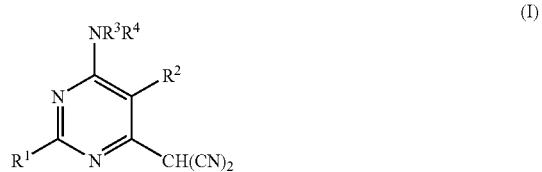

(I)

to processes for their preparation, and to their use as herbicides and plant growth regulators, in particular as herbicides for the selected control of harmful plants in useful plant crops.

15 Claims, No Drawings

PYRIMIDIN-4-YLPROPANEDINITRILE DERIVATIVES, PROCESSES FOR THEIR PREPARATION AND THEIR USE AS HERBICIDES AND PLANT GROWTH REGULATORS

CROSS REFERENCE TO RELATED APPLICATIONS

This application claims priority from European Application No. 09004084.1, filed Mar. 21, 2009, the content of which is incorporated herein by reference in its entirety.

BACKGROUND

1. Field of the Invention

The present invention relates to novel, herbicidally effective pyrimidin-4-ylpropanedinitrile derivatives and to processes for their preparation. The present invention further provides their use as herbicide, in particular as herbicide for the selective control of harmful plants in useful plant crops, and as plant growth regulator alone or in combination with safeners and/or in a mixture with other herbicides.

2. Description of Related Art

It is known from various documents that substituted pyrimidine derivatives have herbicidal and/or pest-controlling properties (see for example WO 2005/063721, WO 2007/082076, and also C. Lamberth, Heterocycles 2006, 68, 3, 561-603 and literature cited therein). However, the active ingredients known from the aforementioned documents have disadvantages upon use, e.g. they have (a) no or an only inadequate herbicidal effect against harmful plants, (b) too small a spectrum of the controlled harmful plants, or (c) too low a selectivity in useful plant crops.

EP 0 136 976 A discloses 2-phenyl-substituted pyrimidines, which are used as growth regulators. However, a herbicidal effect is not disclosed, nor is the substitution pattern according to the invention.

DE 25 20 381 A1 likewise discloses pyrimidine-based plant growth regulators, although these only carry aliphatic hydrocarbon substituents on the pyrimidine.

It is therefore desirable to provide chemical active ingredients which can be used with advantages as herbicides or plant growth regulators.

SUMMARY

Surprisingly, it has now been found that certain substituted pyrimidin-4-ylpropanedinitrile derivatives have good herbicidal effect and at the same time high compatibility towards useful plants. The present invention therefore provides compounds of the formula (I) and N-oxides and agrochemically suitable salts thereof,

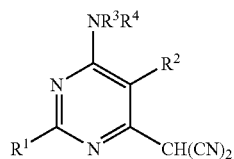

(I)

in which the radicals have the following meaning:

$R^1$ is phenyl, optionally substituted with 1-3 radicals $R^x$, which, independently of one another, are halogen, carboxyl, cyano, nitro, $(C_1-C_6)$alkyl, $(C_1-C_6)$haloalkyl, $(C_1-C_4)$hydroxyalkyl, $(C_2-C_4)$alkoxyalkyl, $(C_2-C_4)$haloalkoxyalkyl, $(C_2-C_4)$alkenyl, $(C_2-C_4)$haloalkenyl, $(C_2-C_4)$alkynyl, $(C_3-C_4)$haloalkynyl, hydroxy, $(C_1-C_4)$alkoxy, $(C_1-C_4)$haloalkoxy, $(C_2-C_4)$alkenyloxy, $(C_2-C_4)$haloalkenyloxy, $(C_2-C_4)$alkynyloxy, $(C_3-C_4)$haloalkynyloxy, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_2-C_4)$alkenylthio, $(C_2-C_4)$haloalkenylthio, $(C_2-C_4)$alkenylsulfinyl, $(C_2-C_4)$haloalkenylsulfinyl, $(C_2-C_4)$alkenylsulfonyl, $(C_2-C_4)$haloalkenylsulfonyl, $(C_2-C_4)$alkynylthio, $(C_3-C_4)$haloalkynylthio, $(C_3-C_4)$alkynylsulfinyl, $(C_3-C_4)$haloalkynylsulfinyl, $(C_3-C_4)$alkynylsulfonyl, $(C_3-C_4)$haloalkynylsulfonyl, $(C_1-C_6)$alkylamino, $(C_2-C_8)$dialkylamino, $(C_2-C_6)$alkylcarbonyl, $(C_2-C_6)$alkoxycarbonyl, $(C_2-C_6)$alkylaminocarbonyl, $(C_3-C_8)$dialkylaminocarbonyl, $(C_3-C_6)$trialkylsilyl, phenyl, phenoxy or a 5- or 6-membered heteroaromatic ring, each phenyl ring, phenoxy ring or 5- or 6-membered heteroaromatic ring optionally substituted with 1-3 substituents independently of one another selected from $R^{28}$; or two adjacent radicals $R^x$ together form a group —$OCH_2O$—, —$CH_2CH_2O$—, —$OCH_2CH_2O$—, —$OCH(CH_3)O$—, —$OC(CH_3)_2O$—, —$OCF_2O$—, —$CF_2CF_2O$—, —$OCF_2CF_2O$— or —CH=CH—CH=CH—; or $(C_1-C_6)$-alkyl, optionally substituted with 1-3 radicals $R^y$, which, independently of one another, are halogen, $(C_2-C_6)$alkenyl, $(C_2-C_6)$haloalkenyl, $(C_1-C_3)$alkoxy, $(C_1-C_2)$haloalkoxy, $(C_1-C_3)$alkylthio, $(C_1-C_2)$haloalkylthio or optionally substituted aryl; or $(C_2-C_6)$-alkenyl, optionally substituted with 1-3 radicals $R^z$, which, independently of one another, are halogen, $(C_1-C_6)$alkyl, $(C_1-C_6)$haloalkyl, $(C_1-C_3)$alkoxy, $(C_1-C_2)$haloalkoxy, $(C_1-C_3)$alkylthio or $(C_1-C_2)$haloalkylthio;

$R^2$ is H, F, Cl, Br, I, CN, $NO_2$, $OR^5$, $SR^6$ or $N(R^7)R^8$; in which $R^5$ is H, $(C_1-C_4)$alkyl or $(C_1-C_3)$haloalkyl, $R^6$ is H, $(C_1-C_4)$alkyl or $(C_1-C_3)$haloalkyl and $R^7$ and $R^8$, independently of one another, are H or $(C_1-C_4)$alkyl;

$R^3$ is H, $(C_1-C_4)$alkyl optionally substituted with 1-2 radicals $R^9$, $(C_2-C_4)$alkenyl optionally substituted with 1-2 radicals $R^{10}$, or $(C_2-C_4)$alkynyl optionally substituted with 1-2 radicals $R^{11}$; or $R^3$ is $C(=O)R^{12}$, $NO_2$, $OR^{13}$, $S(O)_2R^{14}$, $N(R^{15})R^{16}$ or $N=C(R^{17})R^{18}$;

$R^4$ is H, $(C_1-C_4)$alkyl optionally substituted with 1-2 radicals $R^9$, or $C(=O)R^{12}$; or $R^3$ and $R^4$ together form a group —$(CH_2)_4$—, —$(CH_2)_6$—, —$CH_2CH=CHCH_2$— or —$(CH_2)_2O(CH_2)_2$—, each group optionally substituted with 1-2 radicals $R^{19}$; or $R^3$ and $R^4$ together form a group =$C(R^{20})N(R^{21})R^{22}$ or =$C(R^{23})OR^{24}$;

here, each radical $R^9$, $R^{10}$ and $R^{11}$, independently of the others, is halogen, $(C_1-C_3)$alkoxy, $(C_1-C_3)$haloalkoxy, $(C_1-C_3)$alkylthio, $(C_1-C_3)$haloalkylthio, amino, $(C_1-C_3)$alkylamino, $(C_2-C_4)$dialkylamino or $(C_2-C_4)$alkoxycarbonyl;

$R^{12}$ is in each case independently of the others H, $(C_1-C_4)$alkyl, $(C_1-C_3)$haloalkyl, $(C_1-C_4)$alkoxy, phenyl, phenoxy or benzyloxy;

$R^{13}$ is H, $(C_1-C_4)$alkyl, $(C_1-C_3)$haloalkyl or $CHR^{25}C(O)OR^{26}$;

$R^{14}$ is $(C_1-C_4)$alkyl or $(C_1-C_3)$haloalkyl;

$R^{15}$ is H, $(C_1-C_4)$alkyl or $C(=O)R^{27}$;

$R^{16}$ is H or $(C_1-C_4)$alkyl;

$R^{17}$ is H, $(C_1-C_4)$alkyl or phenyl optionally substituted with 1-3 radicals, which, independently of one another, are $CH_3$, Cl or $OCH_3$;

$R^{18}$ is H or $(C_1-C_4)$alkyl; or $R^{17}$ and $R^{18}$ together form a group —$(CH_2)_4$— or —$(CH_2)_5$—;

$R^{19}$ is, in each case independently of the others, halogen, $(C_1-C_3)$alkyl, $(C_1-C_3)$alkoxy, $(C_1-C_3)$haloalkoxy, $(C_1-C_3)$alkylthio, $(C_1-C_3)$haloalkylthio, amino, $(C_1-C_3)$alkylamino, $(C_2-C_4)$dialkylamino or $(C_2-C_4)$alkoxycarbonyl;

$R^{20}$ is H or $(C_1-C_4)$alkyl;

$R^{21}$ and $R^{22}$, independently of one another, are H or $(C_1-C_4)$alkyl; or $R^{21}$ and $R^{22}$ together form a group —$(CH_2)_4$—, —$(CH_2)_5$—, —$CH_2CH$=$CHCH_2$— or —$(CH_2)_2O(CH_2)_2$—;

$R^{23}$ is H or $(C_1-C_4)$alkyl;

$R^{24}$ is $(C_1-C_4)$alkyl;

$R^{25}$ is H, $(C_1-C_4)$alkyl, $(C_1-C_3)$haloalkyl, $(C_1-C_4)$alkoxy, phenyl, phenoxy or benzyloxy;

$R^{26}$ is H, $(C_1-C_4)$alkyl or $(C_1-C_4)$alkoxy;

$R^{27}$ is H, $(C_1-C_4)$alkyl or benzyl; and $R^{28}$ is, in each case independently of the others, halogen, cyano, nitro, $(C_1-C_6)$alkyl, $(C_1-C_6)$haloalkyl, $(C_2-C_4)$alkenyl, $(C_2-C_4)$haloalkenyl, $(C_3-C_4)$alkynyl, $(C_3-C_4)$haloalkynyl, $(C_1-C_4)$alkoxy, $(C_1-C_4)$haloalkoxy, $(C_1-C_4)$alkylthio, $(C_1-C_4)$haloalkylthio, $(C_1-C_4)$alkylsulfinyl, $(C_1-C_4)$alkylsulfonyl, $(C_1-C_4)$alkylamino, $(C_2-C_8)$dialkylamino, $(C_2-C_4)$alkylcarbonyl, $(C_2-C_6)$alkoxycarbonyl, $(C_2-C_6)$alkylaminocarbonyl, $(C_3-C_8)$dialkylaminocarbonyl or $(C_3-C_6)$trialkylsilyl.

DETAILED DESCRIPTION OF A PREFERRED EMBODIMENT

Here, the total number of carbon atoms is always given for the specified radicals, e.g. a dimethylaminocarbonyl radical is a $C_3$ radical.

Preference is given to compounds of the formula (I) in which the radicals have the following meaning:

$R^1$ is phenyl, optionally substituted with 1-3 radicals $R^x$, which, independently of one another, are halogen, carboxyl, cyano, nitro, $(C_1-C_6)$alkyl, $(C_1-C_6)$haloalkyl, $(C_2-C_4)$alkoxyalkyl, $(C_2-C_4)$haloalkoxyalkyl, $(C_2-C_4)$alkenyl, $(C_2-C_4)$haloalkenyl, $(C_2-C_4)$alkynyl, $(C_3-C_4)$haloalkynyl, hydroxy, $(C_1-C_4)$alkoxy, $(C_1-C_4)$haloalkoxy, $(C_1-C_4)$alkylthio, $(C_1-C_4)$haloalkylthio, $(C_1-C_4)$alkylsulfinyl, $(C_1-C_4)$alkylsulfonyl, $(C_1-C_6)$alkylamino, $(C_2-C_8)$dialkylamino, —$OCH_2O$—, —$CH_2CH_2O$—, —$OCH_2CH_2O$—, —$OCH(CH_3)O$—, —$OC(CH_3)_2O$—, —$OCF_2O$—, —$CF_2CF_2O$— or —$OCF_2CF_2O$—, where the eight last-mentioned substituents are formed in each case by two adjacent $R^x$; or $(C_1-C_6)$alkyl, optionally substituted with 1-3 radicals $R^y$, which, independently of one another, are halogen, $(C_2-C_6)$alkenyl, $(C_2-C_6)$haloalkenyl, $(C_1-C_3)$alkoxy, $(C_1-C_2)$haloalkoxy, $(C_1-C_3)$alkylthio, $(C_1-C_2)$haloalkylthio or optionally substituted phenyl; or $(C_2-C_6)$alkenyl, optionally substituted with 1-3 radicals $R^z$, which, independently of one another, are halogen, $(C_1-C_6)$alkyl, $(C_1-C_6)$haloalkyl, $(C_1-C_3)$alkoxy, $(C_1-C_2)$haloalkoxy, $(C_1-C_3)$alkylthio or $(C_1-C_2)$haloalkylthio;

$R^2$ is H, F, Cl, Br, I, CN or $NO_2$;

$R^3$ is H, $(C_1-C_4)$alkyl, $(C_2-C_4)$alkenyl, $(C_2-C_4)$alkynyl, $C(=O)R^{12}$, $OR^{13}$, $N(R^{15})R^{16}$ or $N=C(R^{17})R^{18}$;

$R^4$ is H or $(C_1-C_4)$alkyl, optionally substituted with 1-2 radicals $R^9$, or $C(=O)R^{12}$; or $R^3$ and $R^4$ together form a group —$(CH_2)_4$—, —$(CH_2)_5$—, —$(CH_2)_2O(CH_2)_2$— or =$C(R^{20})N(R^{21})R^{22}$;

here, each radical $R^9$, $R^{10}$ and $R^{11}$, independently of the others, is halogen, $(C_1-C_3)$alkoxy, $(C_1-C_3)$haloalkoxy, $(C_1-C_3)$alkylthio, $(C_1-C_3)$haloalkylthio, amino, $(C_1-C_3)$alkylamino, $(C_2-C_4)$dialkylamino or $(C_2-C_4)$alkoxycarbonyl;

$R^{12}$ is, in each case independently of the others, H, $(C_1-C_4)$alkyl, $(C_1-C_3)$haloalkyl, $(C_1-C_4)$alkoxy, phenyl, phenoxy or benzyloxy;

$R^{13}$ is H, $(C_1-C_4)$alkyl, $(C_1-C_3)$haloalkyl or $CHR^{25}C(O)OR^{26}$;

$R^{15}$ is H, $(C_1-C_4)$alkyl or $C(=O)R^{27}$;

$R^{16}$ is H or $(C_1-C_4)$alkyl;

$R^{17}$ is H, $(C_1-C_4)$alkyl or phenyl optionally substituted with 1-3 radicals which, independently of one another, are $CH_3$, Cl or $OCH_3$;

$R^{18}$ is H or $(C_1-C_4)$alkyl; or $R^{17}$ and $R^{18}$ together form a group —$(CH_2)_4$— or —$(CH_2)_5$—;

$R^{20}$ is H or $(C_1-C_4)$alkyl;

$R^{21}$ and $R^{22}$, independently of one another, are H or $(C_1-C_4)$alkyl; or $R^{21}$ and $R^{22}$ together form a group —$(CH_2)_4$—, —$(CH_2)_5$—, —$CH_2CH$=$CHCH_2$— or —$(CH_2)_2O(CH_2)_2$—;

$R^{25}$ is H, $(C_1-C_4)$alkyl, $(C_1-C_3)$haloalkyl, $(C_1-C_4)$alkoxy, phenyl, phenoxy or benzyloxy; and $R^{26}$ is H, $(C_1-C_4)$alkyl or $(C_1-C_4)$alkoxy.

Particular preference is given to compounds of the formula (I) in which the radicals have the following meaning:

$R^1$ is phenyl, optionally substituted with 1-3 radicals $R^x$, which, independently of one another, are halogen, carboxyl, cyano, nitro, $(C_1-C_6)$alkyl, $(C_1-C_6)$haloalkyl, $(C_1-C_4)$alkoxy, $(C_1-C_4)$haloalkoxy, $(C_1-C_6)$alkylamino, $(C_2-C_8)$dialkylamino, —$OCH_2O$—, —$OCH_2CH_2O$— or —$OCH(CH_3)O$—, where the three last-mentioned substituents are in each case formed by two adjacent $R^x$; or $(C_1-C_6)$alkyl, optionally substituted with 1-3 radicals $R^y$, which, independently of one another, are halogen, $(C_1-C_3)$alkoxy, $(C_1-C_2)$haloalkoxy or unsubstituted phenyl or phenyl substituted by one or more halogens; or $(C_2-C_6)$alkenyl, optionally substituted with 1-3 radicals $R^z$, which, independently of one another, are halogen, $(C_1-C_6)$alkyl, $(C_1-C_6)$haloalkyl, $(C_1-C_3)$alkoxy or $(C_1-C_2)$haloalkoxy;

$R^2$ is F, Cl, Br, I or $NO_2$;

$R^3$ is H, $(C_1-C_4)$alkyl, $(C_2-C_4)$alkenyl, $C(=O)R^{12}$, in which $R^{12}$ is H, $(C_1-C_4)$alkyl, $(C_1-C_3)$haloalkyl, $(C_1-C_4)$alkoxy, phenyl, phenoxy or benzyloxy, or $OR^{13}$, in which $R^{13}$ is H, $(C_1-C_4)$alkyl, $(C_1-C_3)$haloalkyl or $CHR^{25}C(O)OR^{26}$, in which $R^{25}$ is H, $(C_1-C_4)$alkyl, $(C_1-C_3)$haloalkyl, $(C_1-C_4)$alkoxy, phenyl, phenoxy or benzyloxy, and $R^{26}$ is H, $(C_1-C_4)$alkyl or $(C_1-C_4)$alkoxy;

$R^4$ is H or $(C_1-C_4)$alkyl; or $R^3$ and $R^4$ together form a group —$(CH_2)_2O(CH_2)_2$—.

Very particular preference is given to compounds of the formula (I) in which the radicals have the following meaning:

$R^1$ is phenyl, optionally substituted with 1-3 radicals $R^x$, which, independently of one another, are halogen, carboxyl, cyano, nitro, $(C_1-C_6)$alkyl, $(C_1-C_6)$haloalkyl, $(C_1-C_4)$alkoxy, $(C_1-C_4)$haloalkoxy; or $(C_1-C_6)$alkyl, optionally substituted with 1-3 radicals $R^y$, which, independently of one another, are halogen, $(C_1-C_3)$alkoxy, $(C_1-C_2)$haloalkoxy or unsubstituted phenyl or phenyl substituted by a halogen; or $(C_2-C_6)$alkenyl, optionally substituted with 1-3 radicals $R^z$, which, independently of one another, are halogen, $(C_1-C_6)$alkyl, $(C_1-C_6)$haloalkyl, $(C_1-C_3)$alkoxy or $(C_1-C_2)$haloalkoxy;

$R^2$ is F, Cl, Br, I or $NO_2$;

$R^3$ is H, $(C_1\text{-}C_4)$alkyl, $(C_2\text{-}C_4)$alkenyl, $C(=O)R^{12}$, in which $R^{12}$ is H, $(C_1\text{-}C_4)$alkyl, $(C_1\text{-}C_3)$haloalkyl or $(C_1\text{-}C_4)$alkoxy, or $OR^{13}$, in which $R^{13}$ is H, $(C_1\text{-}C_4)$alkyl or $(C_1\text{-}C_3)$haloalkyl; and $R^4$ is H or $(C_1\text{-}C_4)$alkyl.

Particular preference is given to compounds of the formula (I) in which the radicals have the following meaning:

$R^1$ is phenyl, optionally substituted with 1-3 radicals $R^x$, which, independently of one another, are halogen, carboxyl, nitro, $(C_1\text{-}C_6)$alkyl, $(C_1\text{-}C_6)$haloalkyl, $(C_1\text{-}C_4)$alkoxy; or $(C_1\text{-}C_6)$alkyl, optionally substituted with 1-3 radicals $R^y$, which, independently of one another, are halogen, phenyl or 4-halophenyl;

$R^2$ is F, Cl, Br or $NO_2$;

$R^3$ is H or $(C_1\text{-}C_4)$alkyl; and $R^4$ is H or $(C_1\text{-}C_4)$alkyl.

As a result of hydrogen shift, the compounds of the formula (I) can form tautomers, which are likewise provided by the present invention. Thus, for example, the pyrimidin-4-ylpropanedinitrile derivatives (I) may also be present as pyrimidin-4(3H)-ylidenepropanedinitriles (Ia) or as pyrimidin-4(1H) ylidenepropanedinitriles (Ib), with all tautomers being included according to the invention, in particular the forms (I), (Ia) and (Ib).

line, piperidine or pyridine, and also ammonia, ammonium, alkali metal or alkaline earth metal hydroxides, carbonates and hydrogen carbonates, in particular sodium hydroxide and potassium hydroxide, sodium carbonate and potassium carbonate and sodium hydrogen carbonate and potassium hydrogen carbonate. These salts are compounds in which the acidic hydrogen is replaced by a cation suitable for agriculture, for example metal salts, in particular alkali metal salts or alkaline earth metal salts, in particular sodium and potassium salts, or else salts with organic amines or ammonium salts, for example with ammonium ions of the formula $[NRR'R''R''']^+$, in which R, R', R'' and R''' are in each case independently of one another H or an organic radical, in particular $(C_1\text{-}C_6)$ alkyl, $(C_6\text{-}C_{10})$aryl, $(C_7\text{-}C_{20})$aralkyl or $(C_7\text{-}C_{20})$alkylaryl. Examples are $[NH_4]^+$, $[NH_3CH_3]^+$, $[NH_2(CH_3)_2]^+$, $[NH(CH_3)_3]^+$, $[N(CH_3)_4]^+$, $[NH_2CH_3C_2H_5]^+$ or $[NH_2CH_3C_6H_5]^+$. Also suitable are alkylsulfonium and alkylsulfoxonium salts, such as $(C_1\text{-}C_4)$-trialkylsulfonium salts and $(C_1\text{-}C_4)$-trialkylsulfoxonium salts.

The compounds of the formula (I) can form salts through the addition reaction of a suitable inorganic or organic acid, for example mineral acids, such as, for example, HCl, HBr, $H_2SO_4$, $H_3PO_4$ or $HNO_3$, or organic acids, e.g. carboxylic acids, such as formic acid, acetic acid, propionic acid, oxalic acid, lactic acid or salicylic acid, or sulfonic acids, such as, for

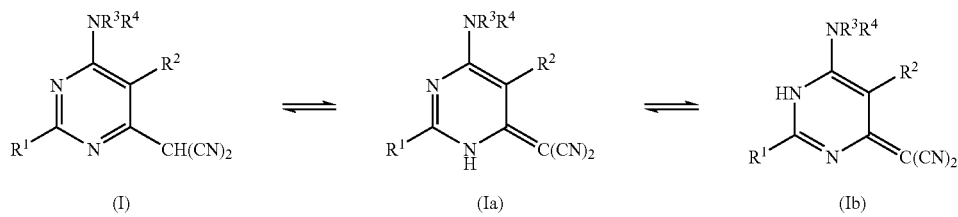

(I)    (Ia)    (Ib)

The compounds of the formula (I) may be present as stereoisomers depending on the type and linkage of the substituents. The possible stereoisomers defined by their specific three-dimensional shape, such as enantiomers, diastereomers, Z and E isomers, geometric isomers and atrope isomers and mixtures thereof are all covered by formula (I).

If, for example, one or more alkenyl groups are present, then diastereomers (Z and E isomers) can arise. If, for example, one or more asymmetric carbon atoms (=asymmetrically substituted carbon atoms) are present and/or asymmetric sulfur atoms are present in the form of sulfoxides which can exist in two enantiomeric forms, then enantiomers and diastereomers can arise. Stereoisomers can be isolated from the mixtures produced during the preparation by customary separation methods, for example by chromatographic separation methods. Likewise, stereoisomers can be selectively prepared through use of stereoselective reactions using optically active starting materials and/or auxiliaries. The invention thus also relates to all stereoisomers which are covered by the formula (I), even if they are not stated with their specific stereo form, and mixtures thereof.

The compounds of the formula (I) can form agrochemically suitable salts. Salt formation can take place in a known manner, e.g. through the action of a base on those compounds of the formula (I) which carry an acidic hydrogen atom, e.g. in the case when $R^1$ contains an OH group or a sulfonamide group $—NHSO_2—$. Salt formation can likewise take place as a result of the action of a base on CH-acidic compounds, such as (substituted) propanedinitriles. Suitable bases are, for example, organic amines, such as trialkylamines, morphoexample, p-toluenesulfonic acid, onto a basic group, such as amino, alkylamino, dialkylamino, piperidino, morpholino or pyridino. These salts then contain the conjugated base of the acid as anion. Suitable substituents which are present in deprotonated form, such as e.g. sulfonic acids, carboxylic acids or CH-acidic groups, such as propanedinitriles, can also form internal salts with groups that are protonatable for their part, such as amino groups.

The compounds of the formula (I) can form N-oxides. The N-oxides can be formed in a known manner e.g. by oxidation of the particular pyrimidines with peroxycarboxylic acids or hydrogen peroxide in solvents such as acetonitrile, dichloromethane, chloroform, acetone. DMF, acetic acid, e.g. at temperatures between 0° and 100° C. (see: S. von Angerer, Science of Synthesis 2003, 16, 548-550 and the literature cited therein in each case).

The compounds of the formula (I) and N-oxides and agrochemically suitable salts thereof are also referred to in short as compounds used according to the invention or compounds according to the invention. The terms used above and hereinbelow are familiar to the person skilled in the art and have in particular the meanings explained below:

An inorganic radical is a radical without carbon atoms, preferably halogen, OH and inorganic salts thereof, in which the H is replaced by a cation, for example alkali metal and alkaline earth metal salts, $—NH_2$ and ammonium salts thereof with (inorganic) acids, for example mineral acids, $—N_3$ (azide), $—N_2^+A^-$ (diazonium group, where A'' is an anion), $—NO$, $—NHOH$, $—NHNH_2$, $—NO_2$, $—ONO$, $—ONO_2$, $—SH$, $—SOH$ (sulfenic acid group), $—S(O)OH$ (sulfinic acid group), —S(O)$_2$OH (or also in short SO$_3$H, sulfonic acid group), —O—SO$_2$H (sulfite group), —O—SO$_3$H (sulfate group), —SO$_2$NH$_2$ (sulfamoyl group), —SO$_2$NHOH (hydroxysulfamoyl group), —NHS(O)OH (sulfinoamino group), —NHS(O)$_2$OH (sulfoamino group), —P(O)(OH)$_2$ (phosphonic acid group), —O—P(OH)$_3$ (phosphate group), —P(O)(NH$_2$)$_2$, —PO(OH)(NH$_2$), —PS(OH)$_2$, —PS(NH$_2$)$_2$ or —PS(OH)(NH$_2$), —B(OH)$_2$ (boronic acid group) and the hydrated or dehydrated forms of the acid groups, and (inorganic) salts thereof; the term "inorganic radical" also includes the hydrogen radical (the hydrogen atom), where this is often in the definitions already a constituent of the unsubstituted base structure of an organic radical (example "unsubstituted phenyl"); the term "inorganic radical" preferably here does not include pseudohalogen groups such as CN, SCN, organic metal complexes, carbonate or COOH which, on account of the content of carbon atoms, are assigned to the organic radicals.

The term "halogen" or "halogen atom" means, for example, fluorine, chlorine, bromine or iodine.

If the term is used for a radical, then "halogen" or "halogen atom" means, for example, a fluorine, chlorine, bromine or iodine atom.

Alkyl is a straight-chain, branched or cyclic hydrocarbon radical. The expression "(C$_1$-C$_4$)alkyl" is for example shorthand for alkyl having one to 4 carbon atoms corresponding to the range stated for carbon atoms and includes e.g. the radicals methyl, ethyl, 1-propyl, 2-propyl, 1-butyl, 2-butyl, 2-methylpropyl, tert-butyl, cyclopropyl and cyclobutyl. General alkyl radicals with a larger stated range of carbon atoms, e.g. "(C$_1$-C$_6$)alkyl", accordingly also include straight-chain, branched or cyclic alkyl radicals with a relatively large number of carbon atoms, i.e. according to example also the alkyl radicals having 5 and 6 carbon atoms.

Unless specifically stated, in the case of the hydrocarbon radicals such as alkyl, alkenyl and alkynyl radicals, and also in composite radicals, preference is given to the lower carbon backbones, e.g. having 1 to 6 carbon atoms or in the case of unsaturated groups having 2 to 6 carbon atoms. Alkyl radicals, also in the composite radicals such as alkoxy, haloalkyl etc., are e.g. methyl, ethyl, cyclo-, n- or isopropyl, cyclo-, n-, iso-, tert- or 2-butyl, pentyls, hexyls, such as cyclohexyl, n-hexyl, isohexyl and 1,3-dimethylbutyl, heptyls, such as cycloheptyl, n-heptyl, 1-methylhexyl and 1,4-dimethylpentyl.

Preferred cyclic alkyl radicals preferably have 3-8 ring carbon atoms, e.g. cyclopropyl, cyclobutyl, cyclopentyl or cyclohexyl. In the case of optionally substituted cyclic alkyl radicals, cyclic systems with substituents are included, where also substituents with a double bond on the cyclic alkyl radical, e.g. an alkylidene group such as methylidene, are included.

In the case of optionally substituted cyclic alkyl radicals, polycyclic aliphatic systems are also included, such as bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl(norbornyl), adamantan-1-yl and adamantan-2-yl.

In the case of optionally substituted cyclic alkyl radicals, spirocyclic aliphatic systems are also included, such as, for example, spiro[2.2]pent-1-yl, spiro[2.3]hex-1-yl, spiro[2.3]hex-4-yl, 3-spiro[2.3]hex-5-yl.

Alkenyl and alkynyl radicals have the meaning of the possible unsaturated straight-chain, branched or cyclic radicals corresponding to the alkyl radicals, where at least one double bond or triple bond is present. Preference is given to radicals with one double bond or with one triple bond.

Alkenyl also includes straight-chain, branched or cyclic hydrocarbon radicals with more than one double bond, such as 1,3-butadienyl, 1,4-pentadienyl or cyclohexadienyl, but also allenyl or cumulenyl radicals with one or more cumulated double bonds, such as, for example, allenyl (1,2-propadienyl), 1,2-butadienyl and 1,2,3-pentatrienyl.

Alkynyl also includes straight-chain, branched or cyclic hydrocarbon radicals with more than one triple bond or else with one or more triple bonds and one or more double bonds, such as, for example, 1,3-butatrienyl or 3-penten-1-yn-1-yl.

Alkenyl is e.g. vinyl, which may be optionally substituted by further alkyl radicals, e.g.
prop-1-en-1-yl, but-1-en-1-yl;
allyl, 1-methylprop-2-en-1-yl, 2-methylprop-2-en-1-yl, but-2-en-1-yl,
1-methylbut-3-en-1-yl and 1-methylbut-2-en-1-yl, 2-methylprop-1-en-1-yl,
1-methylprop-1-en-1-yl, 1-methylprop-2-en-1-yl, 2-methylprop-2-en-1-yl,
but-2-en-1-yl, but-3-en-1-yl, 1-methylbut-3-en-1-yl or 1-methylbut-2-en-1-yl, pentenyl,
2-methylpentenyl or hexenyl.

(C$_2$-C$_6$)-Alkynyl is for example ethynyl, propargyl, 1-methylprop-2-yn-1-yl, 2-butynyl, 2-pentynyl or 2-hexynyl, preferably propargyl, but-2-yn-1-yl, but-3-yn-1-yl or 1-methylbut-3-yn-1-yl.

Cyclic alkenyl radicals area carbocyclic, nonaromatic, partially unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, where substituents with a double bond on the cycloalkenyl radical, e.g. an alkylidene group such as methylidene, are also included. In the case of optionally substituted cycloalkenyl, the explanations for substituted cyclic alkyl radicals apply accordingly.

Alkylidene, e.g. also in the form (C$_1$-C$_{10}$)alkylidene, is the radical of a straight-chain, branched or cyclic hydrocarbon radical which is bonded via a double bond. Suitable binding sites for alkylidene are naturally only positions on the base structure at which two H atoms can be replaced by the double bond; radicals are e.g. =CH$_2$, =CH—CH$_3$, =C(CH$_3$)—CH$_3$, =C(CH$_3$)—C$_2$H$_5$ or =C(C$_2$H$_5$)—C$_2$H$_5$.

Aryl is a mono-, bi- or polycyclic aromatic system having preferably 6 to 14, in particular 6 to 10, ring carbon atoms, for example phenyl, naphthyl, anthryl, phenanthrenyl, and the like, preferably phenyl.

In the case of optionally substituted aryl, polycyclic systems, such as tetrahydronaphthyl, indenyl, indanyl, fluorenyl, biphenylyl, are also included, where the binding site is on the aromatic system. From the point of view of systematics, aryl is generally also covered by the term "optionally substituted phenyl".

Unless stated otherwise, the definition "is substituted with one or more radicals" means, independently of one another, one or more identical or different radicals, where two or more radicals can form one or more rings on a cycle as base structure. Substituted radicals, such as a substituted alkyl, alkenyl, alkynyl, aryl, phenyl, benzyl, heterocyclyl and heteroaryl radical, are, for example, a substituted radical derived from the unsubstituted base structure, where the substituents are, for example, one or more, preferably 1, 2 or 3, radicals from the group halogen, alkoxy, alkylthio, hydroxy, amino, nitro, carboxy or a group equivalent to the carboxy group, cyano, isocyano, azido, alkoxycarbonyl, alkylcarbonyl, formyl, carbamoyl, mono- and dialkylaminocarbonyl, substituted amino, such as acylamino, mono- and dialkylamino, trialkylsilyl and optionally substituted cyclic alkyl, optionally substituted aryl, optionally substituted heterocyclyl, where each of the last-mentioned cyclic groups may also be bonded via heteroatoms or divalent functional groups as in the case of the specified alkyl radicals, and alkylsulfinyl where both enantiomers of the alkylsulfonyl group are included, alkylsulfonyl, alkylphosphinyl, alkylphosphonyl and, in the case of cyclic radicals (="cyclic base structure"), also alkyl, haloalkyl, alkylthioalkyl, alkoxyalkyl, optionally substituted mono- and dialkylaminoalkyl and hydroxyalkyl;
in the term "substituted radicals" such as substituted alkyl (e.g. straight-chain, branched or cyclic alkyl) etc., included substituents in addition to the specified saturated hydrocarbon-containing radicals are corresponding unsaturated aliphatic and aromatic radicals such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and dialkenylaminocarbonyl, mono- and dialkynylaminocarbonyl, mono- and dialkenylamino, mono- and dialkynylamino, trialkenylsilyl, trialkynylsilyl, phenyl, phenoxy etc. In the case of substituted cyclic radicals with aliphatic moieties in the ring, also included are cyclic systems with those substituents which are bonded to the ring with a double bond, e.g. are substituted with an alkylidene group such as methylidene or ethylidene or an oxo group, imino group or substituted imino group.

If two or more radicals form one or more rings, then these may be carbocyclic, heterocyclic, saturated, partially saturated, unsaturated, for example also aromatic and optionally further substituted. The fused rings are preferably 5- or 6-membered rings, particular preference being given to benzofused cycles.

The substituents specified by way of example ("first substituent level") can, if they contain hydrocarbon-containing moieties, be therein optionally further substituted ("second substituent level"), for example by one of the substituents as is defined for the first substituent level. Corresponding further substituent levels are possible. Preferably, only one or two substituent levels are covered by the term "substituted radical".

Preferred substituents for the substituent levels are, for example, amino, hydroxy, halogen, nitro, cyano, isocyano, mercapto, isothiocyanato, carboxy, carboxamide, $SF_5$, aminosulfonyl, alkyl, alkenyl, alkynyl, monoalkylamino, dialkylamino, N-alkanoylamino, alkoxy, alkenyloxy, alkynyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, alkenylthio, alkynylthio, alkylsulfenyl, alkylsulfinyl, where both enantiomers of the alkylsulfinyl group are included, alkylsulfonyl, monoalkylaminosulfonyl, dialkylaminosulfonyl, alkylphosphinyl, alkylphosphonyl, where for alkylphosphinyl and alkylphosphonyl both enantiomers are included, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino, benzylamino, heterocyclyl and trialkylsilyl.

Substituents which are composed of two or more substituent levels are preferably, for example, alkoxyalkyl, such as monoalkoxyalkyl or dialkoxyalkyl, alkylthioalkyl, alkylthioalkoxy, alkoxyalkoxy, such as monoalkoxyalkoxy or dialkoxyalkoxy, benzyl, phenethyl, benzyloxy, haloalkyl, haloalkoxy, haloalkylthio, haloalkanoyl, haloalkylcarbonyl, haloalkoxycarbonyl, haloalkoxyalkoxy, haloalkoxyalkylthio, haloalkoxyalkanoyl, haloalkoxyalkyl, alkanoylalkyl, haloalkanoylalkyl, alkanoyloxyalkyl.

For radicals with carbon atoms, preference is given to those with 1 to 6 carbon atoms, preferably 1 to 4 carbon atoms, in particular 1 or 2 carbon atoms. As a rule, preference is given to substituents from the group halogen, e.g. fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference here is given to the substituents methyl, methoxy, fluorine and chlorine.

Substituted amino such as mono- or disubstituted amino means a radical from the group of the substituted amino radicals which are N-substituted for example by one or two identical or different radicals from the group alkyl, hydroxy, amino, alkoxy, acyl and aryl; preferably mono- and dialkylamino, mono- and diarylamino, such as optionally substituted anilines, acylamino, N,N-diacylamino, N-alkyl-N-arylamino, N-alkyl-N-acylamino, and saturated N-heterocycles; preference is given here to alkyl radicals having 1 to 4 carbon atoms; aryl here is preferably phenyl or substituted phenyl; for acyl, the definition given below applies, preferably $(C_1-C_4)$alkanoyl. The same applies for substituted hydroxylamino or hydrazino.

Substituted amino also includes quaternary a onium compounds (salts) with four organic substituents on the nitrogen atom.

A group equivalent to the carboxy group is for example an alkyl ester, aryl ester, O-alkylthio ester, S-alkyldithio ester, S-alkylthio ester, carboximide ester, carboximidethio ester; 5,6-dihydro-1,2,4-dioxazin-3-yl; 5,6-dihydro-1,2,4-oxathiazin-3-yl, trialkyl orthoesters, dialkoxyalkylamino esters, dialkylaminoalkoxy esters, trialkylamino esters, amidines, dialkoxyketene acetals or dialkyldithioketene acetals.

Optionally substituted phenyl is preferably phenyl which is unsubstituted or substituted one or more times, preferably up to three times, by identical or different radicals from the group halogen, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl, $(C_1-C_4)$haloalkoxy, $(C_1-C_4)$alkylthio, $(C_1-C_4)$haloalkylthio, cyano, isocyano and nitro, e.g. o-, m- and p-tolyl, dimethylphenyls, 2-, 3- and 4-chlorophenyl, 2-, 3- and 4-fluorophenyl, 2-, 3- and 4-trifluoromethyl and -trichloromethylphenyl, 2,4-, 3,5-, 2,5- and 2,3-dichlorophenyl, o-, m- and p-methoxyphenyl.

Optionally substituted heterocyclyl is preferably heterocyclyl which is unsubstituted or substituted one or more times, preferably up to three times, by identical or different radicals from the group halogen, cyano, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl, $(C_1-C_4)$haloalkoxy, nitro and oxo, in particular one or more times by radicals from the group halogen, $(C_1-C_4)$alkyl, $(C_1-C_4)$alkoxy, $(C_1-C_4)$haloalkyl and oxo, very particularly by one or two $(C_1-C_4)$alkyl radicals.

Haloalkyl, -alkenyl and -alkynyl are alkyl, alkenyl or alkynyl partially or completely substituted by identical or different halogen atoms, e.g. monohaloalkyl such as $CH_2CH_2Cl$, $CH_2CH_2F$, $CHClCH_3$, $CHFCH_3$, $CH_2Cl$, $CH_2F$; perhaloalkyl such as $CCl_3$ or $CF_3$ or $CF_2CF_3$; polyhaloalkyl such as $CHF_2$, $CH_2F$, $CH_2CHFCl$, $CHCl_2$, $CF_2CF_2H$, $CH_2CF_3$; haloalkoxy is e.g. $OCF_3$, $OCHF_2$, $OCH_2F$, $OCF_2CF_3$, $OCH_2CF_3$ and $OCH_2CH_2Cl$; the same applies for haloalkenyl and other radicals substituted by halogen.

An organic acid radical is a radical of an oxo acid or thioacid of the formula

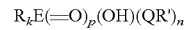

where
R is an organic radical,
E is an atom from the group C, S, P,
Q independently of the others is an atom or a molecule fragment from the group O, S, NR' and
R' independently of the others is a hydrogen atom, alkyl, haloalkyl, alkoxyalkyl or optionally aryl,
k, p are natural numbers, k=1, 2; p=0-2;
n is a natural number or zero.

The organic acid radical is produced formally by separating off an hydroxy group on the acid function, where the organic radical R in the acid may also be joined to the acid function via one or more heteroatoms:

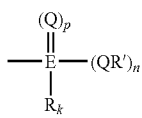

For oxo acids of carbon, this is described in the IUPAC Compendium of Chemical Terminology (1997).

Examples of organic acid radicals which are derived from the oxo acids or thio acids of sulfur (E=S), are $S(O)OCH_3$, $SO_2OH$, $SO_2OCH_3$ or $SO_2NHR$ (N-substituted sulfonamide acids).

In the case of k=1, alkylsulfonyl and alkylsulfinyl radicals, such as e.g. $(H_3C)S(O)_2$, $(F_3C)S(O)_2$, p-tolyl$S(O)_2$, $(H_3C)S(O)(NH$-n-$C_4H_9)$, $(C_6H_5)S(S)(O)$ or $(C_6H_5)S(O)$ are also included.

Examples of organic acid radicals which are derived from the oxo acids or thio acids of phosphorus (E=P) are radicals derived from phosphinic acid and phosphonic acid, where these radicals may be further esterified, e.g. $-PO(OCH_3)_2$, $(C_2H_5O)P(O)OH$, $(C_2H_5O)P(O)(SC_6H_5)$, $(H_3CO)P(O)NH(C_6H_5)$ or $-PO(NMe_2)_2$. In the case of k=1, alkylphosphinyl and alkylphosphonyl radicals, such as e.g. $(H_3C)_2P(O)$, $(C_6H_5)_2P(O)$, $(H_3C)(C_6H_5)P(O)$; $(H_3C)P(O)OCH_3$, $(H_5C_2)P(O)(OC_2H_5)$, $(C_6H_5)P(O)(OC_2H_5)$, $(C_2H_5)P(O)(SC_6H_5)$, $(H_3C)P(O)NH(C_6H_5)$, $(H_3C)P(S)(NH$-1-$C_3H_7)$, $(C_6H_5)P(S)(OC_2H_5)$ or $(C_6H_5)P(S)(SC_2H_5)$ are also included.

Organic acid radicals which are derived from the oxo acids of carbon (E=C, Q=O) are also referred to in a narrower sense by the term "acyl".

Examples of acyl are the radical —CO—R of a carboxylic acid HO—CO—R and radicals of acids derived therefrom or the radical of carbonic acid monoesters or N-substituted carbamic acids and also carbonates and esters thereof.

Acyl is, for example, formyl, oxalyl (ester), alkylcarbonyl such as [($C_1$-$C_4$)alkyl]carbonyl, haloalkylcarbonyl, phenylcarbonyl, alkyloxycarbonyl, specifically tert-butyloxycarbonyl, phenyloxycarbonyl, benzyloxycarbonyl, fluorenyloxycarbonyl, N-alkyl-1-iminoalkyl, N-alkyl- and N,N-dialkylcarbamoyl. Here, the radicals may in each case be yet further substituted in the alkyl or phenyl moiety, for example in the alkyl moiety by one or more radicals from the group halogen, cyano, alkoxy, phenyl and phenoxy; examples of substituents in the phenyl moiety are the substituents already mentioned above in general terms for substituted phenyl.

Acyl is preferably an acyl radical in the narrower sense, i.e. a radical of an organic acid in which the acid group is directly bonded to the carbon atom of an organic radical, for example alkanoyl, such as formyl or acetyl, aroyl such as phenylcarbonyl, and other radicals of saturated or unsaturated organic acids.

"Aroyl" is an aryl radical as defined above which is bonded via a carbonyl group, e.g. the benzoyl group.

If a general radical is defined as "hydrogen", this is a hydrogen atom.

The "yl position" of a radical refers to its binding site.

The present invention also provides methods for the preparation of the compounds according to the invention. The compounds according to the invention can alternatively be synthesized by different processes.

In the processes below, solvents are partially used. In this connection, "inert solvents" refer in each case to solvents which are inert under the particular reaction conditions, but do not have to be inert under any reaction conditions.

Compounds of the formula (I) can be prepared e.g. by reacting the corresponding halogen compounds (II) with the particular amine of the formula (III), optionally using an organic or inorganic base (e.g. triethylamine, pyridine, potassium carbonate, sodium carbonate). The reaction can be carried out in various solvents such as methanol, ethanol, dioxane, THF, dichloromethane, DMSO, DMF and water. The reaction temperatures are generally between 20° C. and 180° C. depending on the amine used.

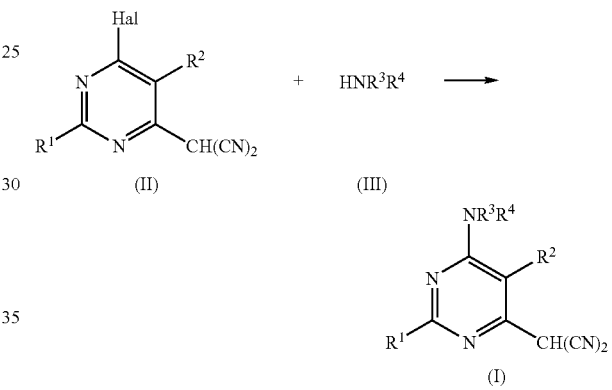

Compounds of the formula (II) can be obtained e.g. by reacting the corresponding 4,6-dihalogen compounds (IV) with the respective alkali metal salt of malonodinitrile. The respective salts can be generated e.g. in situ by treating malonodinitrile with various bases such as e.g. n-butyllithium, lithium diisopropylamide, sodium hydride or potassium carbonate at temperatures between −80° C. and 80° C. After adding the 4,6-dihalopyrimidines (IV), the reaction is carried out in a temperature range between 0° C. and 100° C., preferably in aprotic solvents such as THF, DMSO, DMF or dioxane.

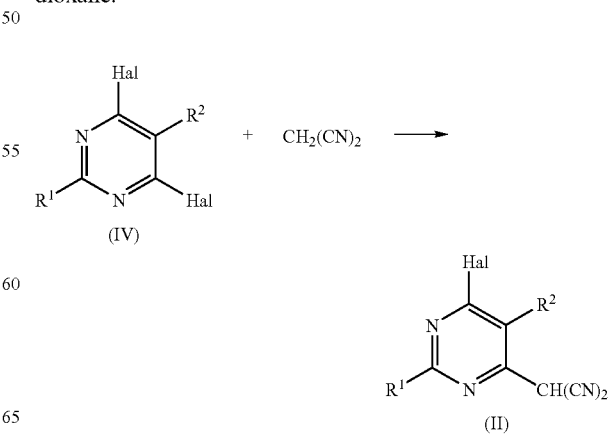

The preparation of compounds of the formula (IV) takes place by generally known methods: K. Findeisen, K. Wagner, Synthesis 1978, 40-42; H. Gershon, K. Dittmer, R. Braun, J. Org. Chem. 1961, 26, 1874-1877; H. Gershon, R. Braun, A. Scala, R. Rodin, J. Med. Chem. 1964, 7, 808-811; D. T. Hurst, Heterocycles 1984, 22, 79-84; L. Provins et al., Bioorg. Med. Chem. Lett. 2006, 16, 1834-1839; T. Sakamoto, Y. Kondo, R. Watanabe, H. Yamanaka, Chem. Pharm. Bull. 1986, 34, 2719-2724; S. von Angerer. Science of Synthesis 2003, 16, 379-572 and the literature cited therein in each case. In the formulae (II), (III) and (IV), the radicals $R^1$, $R^2$, $R^3$ and $R^4$ have the same meaning as in formula (I). Hal in formulae (II) and (IV) is a halogen atom, where, in the case of two or more Hal in formula (IV), in each case different halogens may be present.

Collections of compounds according to the invention which can be synthesized by the aforementioned reactions can also be prepared in a parallel manner, it being possible for this to take place in a manual, partially automated or completely automated manner. In this connection, it is possible, for example, to automate the reaction procedure, the work-up or the purification of the products and/or intermediates. Overall, this is understood as meaning a procedure as described, for example, by D. Tiebes in Combinatorial Chemistry—Synthesis, Analysis, Screening (editor Günther Jung), Verlag Wiley 1999, on pages 1 to 34.

For the parallel reaction procedure and work-up, a series of commercially available instruments can be used, for example Calypso reaction blocks from Barnstead International, Dubuque, Iowa 52004-0797, USA or reaction stations from Radleys, Shirehill, Saffron Walden, Essex, CB11 3AZ, England or MultiPROBE Automated Workstations from Perkin Elmar, Waltham, Mass. 02451, USA. For parallel purification of compounds according to the invention or of intermediates produced during the preparation, chromatography apparatuses inter alia are available, for example from ISCO, Inc., 4700 Superior Street, Lincoln, Nebr. 68504, USA.

The listed apparatuses lead to a modular procedure in which the individual steps are automated, but manual operations have to be carried out between the steps. This can be circumvented by using partially or completely integrated automated systems in which the particular automated modules are operated for example by robots. Automated systems of this type can be obtained for example from Caliper, Hopkinton, Mass. 01748, USA.

The implementation of one or more synthesis steps can be supported through the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described here, the preparation of compounds according to the invention can take place completely or partially by solid-phase-supported methods. For this purpose, individual intermediates or all intermediates in the synthesis or in a synthesis adapted to the corresponding procedure are bonded to a synthesis resin. Solid-phase-supported synthesis methods are described adequately in the specialist literature, e.g. Barry A. Bunin in "The Combinatorial Index", Verlag Academic Press, 1998 and Combinatorial Chemistry—Synthesis, Analysis, Screening (editor Günther Jung), Verlag Wiley, 1999. The use of solid-phase-supported synthesis methods permits a series of protocols known in the literature, which in turn can be carried out manually or automated. The reactions can be carried out for example by means of IRORI technology in microreactors from Nexus Biosystems, 12140 Community Road, Poway, Calif. 92064, USA.

Both on solid phase and also in liquid phase, the implementation of one or more synthesis steps can be supported through the use of microwave technology. The specialist literature describes a series of experimental protocols, for example in Microwaves in Organic and Medicinal Chemistry (editors C. O. Kappe and A. Stadler), Verlag Wiley, 2005.

The preparation according to the processes described here produces compounds according to the invention in the form of substance collections which are called libraries. The present invention also provides libraries which contain at least two compounds according to the invention.

The compounds according to the invention have excellent herbicidal effectiveness against a broad spectrum of economically important mono- and dicotyledonous annual harmful plants. Difficult-to-control perennial harmful plants which produce shoots from rhizomes, root stocks or other perennial organs, are also well controlled by the active ingredients.

The present invention therefore also provides a method for controlling undesired plants or for regulating the growth of plants, preferably in plant crops, in which one or more compound(s) according to the invention are applied to the plants (e.g. harmful plants such as mono- or dicotyledonous weeds or undesired crop plants), the seed material (e.g. grains, seeds or vegetative propagation organs such as tubers or shoot parts with buds) or the area on which the plants grow (e.g. the area under cultivation). Here, the compounds according to the invention can be applied e.g. in the presowing method (optionally also through incorporation into the soil), pre-emergence method or post-emergence method. Specifically, examples which may be mentioned are some of the representatives of mono- and dicotyledonous weed flora which can be controlled by the compounds according to the invention, without a limitation to certain species being intended through the naming.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous harmful plants of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the earth's surface prior to germination, then either the weed seedlings are prevented completely from emerging, or the weeds grow until they have reached the seed-leaf stage, but then their growth stops and finally, after three to four weeks have elapsed, they die completely.

If the active ingredients are applied post-emergence to the green parts of the plants, growth likewise stops following treatment and the harmful plants remain at the growth stage at the time of application, or they die completely after a certain time, so that in this manner competition by the weeds, which is harmful to the crop plants, is eliminated very early on and in a lasting manner.

Although the compounds according to the invention have excellent herbicidal activity in respect of mono- and dicotyledonous harmful plants, crop plants of economically important crops such as dicotyledonous crops, e.g. of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops e.g. of the genera *Allium, Ananas, Asparagus, Avena, Hordeum, Oryza, Panicum, Saccharum, Secale, Sorghum, Triticale, Triticum, Zea*, in particular *Zea* and *Triticum*, are only damaged negligibly, if at all, depending on the structure of the particular compound according to the invention and its rate of application. For these reasons, the compounds according to the invention are very highly suitable for the selective control of undesired plant growth in plant crops such as agricultural useful plantations or ornamental plantations.

Moreover, the compounds according to the invention (depending on their particular structure and the application rate applied) have excellent growth regulatory properties in respect of crop plants. They intervene in a plant's metabolism in a regulatory fashion and can thus be used for the targeted influencing of plant ingredients and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays a large role in many monocotyledonous and dicotyledonous crops, allowing lodging to be reduced or prevented completely.

On account of their herbicidal and plant growth regulatory properties, the compounds according to the invention can also be used for controlling harmful plants in crops of known plants or genetically modified plants which are yet to be developed. As a rule, the transgenic plants are distinguished by particularly advantageous properties, for example by resistances to certain pesticides, primarily certain herbicides, resistances to plant diseases or pathogens of plant diseases, such as certain insects or microorganisms such as fungi, bacteria or viruses. Other particular properties relate, for example, to the harvested material with respect to quantity, quality, storability, composition and specific ingredients. For example, transgenic plants with increased starch content or modified quality of the starch or those with a different fatty acid composition of the harvested material are known. Further particular properties can lie in a tolerance or resistance to abiotic stress factors, for example heat, cold, drought, salt and ultraviolet radiation.

Preference is given to using the compounds according to the invention in economically important transgenic crops of useful plants and ornamental plants, for example of cereals such as wheat, barley, rye, oats, millet, rice, manioc and corn, or else crops of sugarbeet, cotton, soybean, rapeseed, potatoes, tomatoes, peas and other vegetable varieties.

Preferably, the compounds according to the invention can be used as herbicides in crops of useful plants which are resistant to, or have been rendered genetically resistant to, the phytotoxic effects of the herbicides.

Conventional ways of producing new plants which have modified properties compared to existing plants consist, for example, in classic cultivation methods and the generation of mutants. Alternatively, new plants with modified properties can be produced using genetic engineering methods (see, e.g. EP 0221044, EP 0131624). For example, in several cases the following have been described genetic modifications of crop plants for the purpose of modifying the starch synthesized in the plants (e.g. WO 92/011376 A, WO 92/014827 A, WO 91/019806 A), transgenic crop plants which are resistant to certain herbicides of the glufosinate type (cf. e.g. EP 0 242 236 A, EP 0 242 246 A) or of the glyphosate type (WO 92/000377 A) or of the sulfonyl urea type (EP 0 257 993 A, U.S. Pat. No. 5,013,659) or to combinations or mixtures of these herbicides through "gene stacking", such as transgenic crop plants e.g. corn or soybean with the tradename or the name Optimum™ GAT™ (glyphosate ALS tolerant).

transgenic crop plants, for example cotton, with the ability to produce *Bacillus thuringiensis* toxins (Bt toxins) which make the plants resistant to certain pests (EP 0 142 924 A, EP 0 193 259 A).

transgenic crop plants with a modified fatty acid composition (WO 91/013972 A).

genetically modified crop plants with new ingredients or secondary substances, e.g. new phytoalexins, which bring about increased resistance to disease (EP 0 309 862 A, EP 0 464 461 A)

genetically modified plants with reduced photorespiration which have higher yields and higher stress tolerance (EP 0 305 398 A)

transgenic crop plants which produce pharmaceutically or diagnostically important proteins ("molecular pharming")

transgenic crop plants distinguished by higher yields or better quality transgenic crop plants distinguished by combinations e.g. of the aforementioned new properties ("gene stacking").

Numerous molecular biological techniques with which new transgenic plants with modified properties can be produced are known in principle; see e.g. I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431).

For genetic manipulations of this kind, nucleic acid molecules which permit a mutagenesis or a sequence modification by recombination of DNA sequences can be introduced into plasmids. For example, with the help of standard methods, it is possible to carry out base exchanges, to remove part sequences or to add natural or synthetic sequences. For joining the DNA fragments to one another, adaptors or linkers may be added to the fragments, see e.g. Sambrook et al., 1989, Molecular Cloning, A Laboratory Manual, 2nd edition, Cold Spring Harbor Laboratory Press, Cold Spring Harbor, N.Y.; or Winnacker "Gene und Klone [Genes and Clones]", VCH Weinheim 2nd edition, 1996.

The preparation of plant cells with reduced activity of a gene product can be achieved, for example, through the expression of at least one corresponding antisense-RNA, a sense-RNA to achieve a cosuppression effect or the expression of at least one correspondingly constructed ribozyme which specifically cleaves transcripts of the aforementioned gene product.

To this end, it is possible to use firstly DNA molecules which encompass the entire coding sequence of a gene product including any flanking sequences which may be present, and also DNA molecules which only encompass parts of the coding sequence, it being necessary for these parts to be long enough to bring about an antisense effect in the cells. Also possible is the use of DNA sequences which have a high degree of homology to the coding sequences of a gene product but are not entirely identical thereto.

During the expression of nucleic acid molecules in plants, the synthesized protein can be localized in any compartment of the plant cell. However, in order to achieve localization in a certain compartment, it is possible, for example, to link the coding region with DNA sequences which ensure localization in a certain compartment. Sequences of this type are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The expression of the nucleic acid molecules can also take place in the organelles of the plant cells.

The transgenic plant cells can be regenerated by known techniques to give whole plants. In principle, the transgenic plants may be plants of any desired plant species, i.e. either monocotyledonous or dicotyledonous plants.

Transgenic plants are thus obtainable which have modified properties as a result of overexpression, suppression or inhibition of homologous (=natural) genes or gene sequences or expression of heterologous (=foreign) genes or gene sequences.

The compounds according to the invention can preferably be used in transgenic crops which are resistant to growth regulators, such as, for example, 2,4 D, dicamba or to herbicides which inhibit essential plant enzymes, e.g. acetolactate synthases (ALS), EPSP synthases, glutamine synthases (GS) or hydroxyphenylpyruvate dioxygenases (HPPD), or to herbicides from the group of sulfonylureas, glyphosates, glufosinates or benzoylisoxazoles and analogous active ingredients, or to any desired combinations of these active ingredients.

The compounds according to the invention can be particularly preferably used in transgenic crop plants which are resistant to a combination of glyphosates and glufosinates, glyphosates and sulfonylureas or imidazolinones. The compounds according to the invention can very particularly preferably be used in transgenic crop plants such as e.g. corn or soybean with the tradename or the name Optimum™ GAT™ (glyphosate ALS tolerant).

When using the compounds according to the invention in transgenic crops, besides the effects against harmful plants that are observed in other crops, effects often arise which are specific to the application in the particular transgenic crop, for example a modified or specifically expanded weed spectrum which can be controlled, modified rates of application which can be used for the application, preferably good combinability with the herbicides against which the transgenic crop is resistant, and also influencing of growth and yield of the transgenic crop plants.

The invention therefore also provides the use of the compounds according to the invention as herbicides for controlling harmful plants in transgenic crop plants.

The compounds according to the invention can be applied e.g. in the form of wettable powders, emulsifiable concentrates, sprayable solutions, dusting agents or granules in the customary preparations. The invention therefore also provides herbicidal and plant growth regulating compositions which comprise the compounds according to the invention.

The compounds according to the invention can be formulated in different ways depending on which biological and/or chemical-physical parameters are prescribed. Suitable formulation options are, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting agents (DP), seed dressings, granules for scattering and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in: "Chemische Technologie [Chemical Technology]", Volume 7, C. Hanser Verlag Munich, 4th edition, 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries such as inert materials, surfactants, solvents and further additives are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte [Surface-active ethylene oxide adducts]", Wiss. Verlagsgesell., Stuttgart 1976; Winnacker-Küchler, "Chemische Technologie [Chemical Technology]", Volume 7, C. Hanser Verlag Munich, 4th edition 1986.

On the basis of these formulations, it is also possible to prepare combinations with other pesticidally active substances, such as, for example, insecticides, acaricides, herbicides, fungicides, and also with safeners, fertilizers and/or growth regulators, e.g. in the form of a ready mix or as tank mix.

Wettable powders are preparations which can be dispersed uniformly in water and which comprise, besides the active ingredient, apart from a diluent or inert substance, also surfactants of ionic and/or nonionic type (wetting agents, dispersants), e.g. polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate and also sodium oleoylmethyltaurate. To prepare the wettable powders, the herbicidal active ingredients are finely ground, for example in customary apparatuses such as hammer mills, blowing mills and air-jet mills, and are mixed simultaneously or subsequently with the formulation auxiliaries.

Emulsifiable concentrates are prepared by dissolving the active ingredient in an organic solvent, e.g. butanol, cyclohexanone, dimethylformamide, xylene or else higher-boiling aromatics or hydrocarbons or mixtures of the organic solvents with the addition of one or more surfactants of ionic and/or nonionic type (emulsifiers). Emulsifiers which can be used are, for example: alkylarylsulfonic calcium salts, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, such as e.g. sorbitan fatty acid esters, or polyoxyethylene sorbitan esters, such as, for example, polyoxyethylene sorbitan fatty acid esters.

Dusting agents are obtained by grinding the active ingredient with finely divided solid substances, e.g. talc, natural clays, such as kaolin, bentonite and pyrophyllite, or diatomaceous earth.

Suspension concentrates may be water-based or oil-based. They can be produced, for example, by wet grinding by means of standard commercial bead mills and if appropriate addition of surfactants, as have e.g. already been listed above in connection with the other types of formulation.

Emulsions, e.g. oil-in-water emulsions (EW), can be prepared, for example, by means of stirrers, colloid mills and/or static mixers using aqueous organic solvents and if appropriate surfactants, as have for example already been listed above in connection with the other types of formulation.

Granules can be prepared either by atomizing the active ingredient onto granulated inert material that is capable of adsorption or by applying active ingredient concentrates by means of adhesives, e.g. polyvinyl alcohol, sodium polyacrylate or else mineral oils, onto the surface of carrier substances such as sand, kaolinites or of granulated inert material. Suitable active ingredients can also be granulated in the manner customary for producing fertilizer granules—if desired in a mixture with fertilizers.

Water-dispersible granules are usually prepared by customary methods such as spray-drying, fluidized-bed granulation, pan granulation, mixing with high-speed mixers and extrusion without solid inert material.

For the preparation of pan granules, fluidized-bed granules, extruder granules and spray granules, see e.g. methods in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8-57.

For further details relating to the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations comprise generally 0.1 to 99% by weight, in particular 0.1 to 95% by weight, of compounds according to the invention. In wettable powders, the active ingredient concentration is, for example about 10 to 90% by weight, the remainder to 100% by weight consists of customary formulation constituents. In the case of emulsifiable concentrates, the active ingredient concentration is about 1 to 90, preferably 5 to 80% by weight. Dust-like formulations comprise 1 to 30% by weight of active ingredient, preferably in most cases 5 to 20% by weight of active ingredient, sprayable solutions comprise about 0.05 to 80, preferably 2 to 50% by weight of active ingredient. In the case of water-dispersible granules, the active ingredient content depends partly on whether the active compound is present in liquid or solid form and which granulation auxiliaries, fillers etc. are used. In the case of the water-dispersible granules, the content of active ingredient is, for example, between 1 and 95% by weight, preferably between 10 and 80% by weight.

In addition, the specified active ingredient formulations optionally comprise the adhesives, wetting agents, dispersants, emulsifiers, penetration agents, preservatives, antifreezes and solvents, fillers, carriers and dyes, antifoams, evaporation inhibitors and agents which influence the pH and the viscosity that are customary in each case.

Suitable combination partners for the compounds according to the invention in mixture formulations or in the tank mix are, for example, known active ingredients, such as insecticides, fungicides, plant growth regulators or herbicides. Examples of such herbicides which can be used are those based on an inhibition of, for example, acetolactate synthase, acetyl-CoA-carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as are described, for example, in Weed Research 26 (1986) 441-445 or "The Pesticide Manual", 14th edition, The British Crop Protection Council and the Royal Soc. of Chemistry, 2003 and literature cited therein. Known herbicides or plant growth regulators which can be combined with the compounds according to the invention are, for example, the following active ingredients (the compounds are referred to either by the "common name" in accordance with the International Organization for Standardization (ISO) or by the chemical name or by the code number) and always encompass all of the application forms such as acids, salts, esters and isomers such as stereoisomers and optical isomers. Here, by way of example, one and sometimes also more application forms are specified:

acetochlor, acibenzolar, acibenzolar-5-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrochlor, aminopyralid, amitrole, ammonium sulfamate, ancymidol, anilofos, asulam, atrazine, azafenidin, azimsulfuron, aziprotryn, BAH-043, BAS-140H, BAS-693H, BAS-714H, BAS-762H, BAS-776H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron. DNOC, eglinazine-ethyl, endothal. EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl] ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate P, glufosinate-P-ammonium, glufosinate-P-sodium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HW-02, imazamethabenz, imazamethabenz-methyl, imazamox, imazapic, imazapyr, imazaquin, imazethapyr, imazosulfuron, inabenfide, indanofan, indaziflam, indole acetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, methazole, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monuron. MT 128, MT-5950, i.e. N-[3-chloro-4-(1-methylethyl)phenyl]-2-methylpentanamide, NGGC-011, naproanilide, napropamide, naptalam. NC-310, i.e. 4-(2,4-dichlorobenzoyl)-1-methyl-5-benzyloxypyrazole, NC-620, neburon, nicosulfuron, nipyraclofen, nitralin, nitrofen, nitrophenolat-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, sulcotrione, sulfallate (CDEC), sulfentrazone, sulfometuron, sulfometuron-methyl, sulfosate (glyphosate-trimesium), sulfosulfuron, SYN-449, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and the following compounds

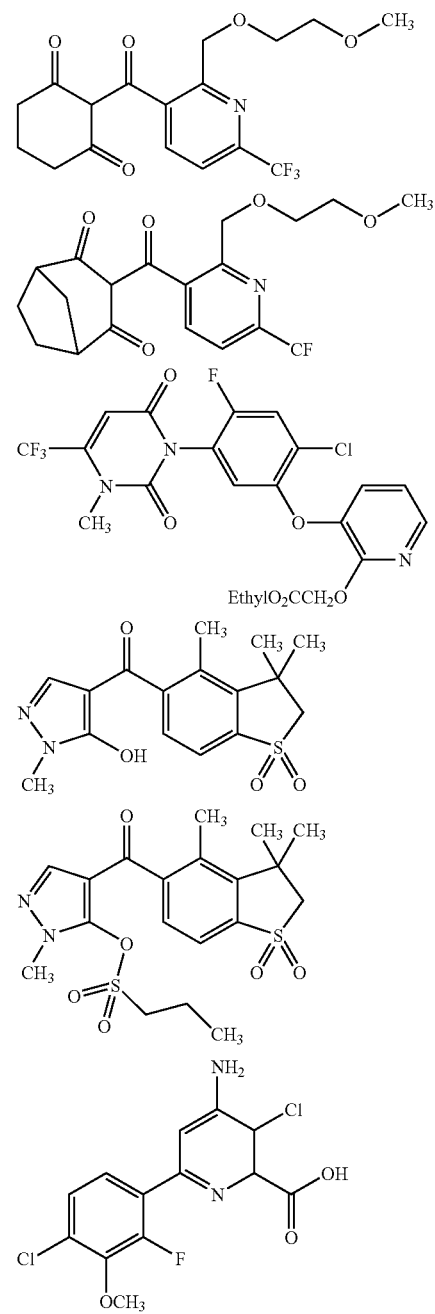

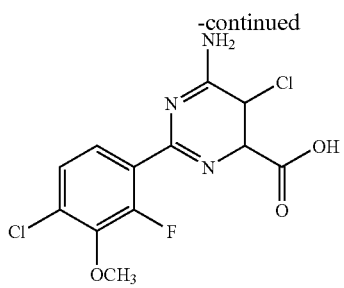

Of particular interest is the selective control of harmful plants in crops of useful plants and ornamental plants. Although the compounds according to the invention already have very good to adequate selectivity in many crops, it is in principle possible, in some crops and primarily also in the case of mixtures with other herbicides which are less selective, for phytotoxicities to occur on the crop plants. Of particular interest in this connection are combinations which comprise the compounds according to the invention in combination with safeners, and optionally further pesticides such as herbicides. The safeners, which are used in an antidotically effective content, reduce the phytotoxic side-effects of the pesticides used, e.g. in economically important crops such as cereals (e.g. wheat, barley, rye, corn, rice, millet), sugarbeet, sugarcane, rapeseed, cotton and soybean, preferably cereals.

The following groups of compounds are for example suitable as safeners:

S1) compounds from the group of heterocyclic carboxylic acid derivatives:

S1$^a$) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds, as described in WO-A-91/07874;

S1$^b$) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds, as described in EP-A-333 131 and EP-A-269 806;

S1$^c$) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds, as described, for example, in EP-A-268554;

S1$^d$) compounds of the triazolecarboxylic acid type (S1$^d$), preferably compounds such as fenchlorazole(-ethyl), i.e.

ethyl 1-(2,4-dichlorophenyl)-5-trichloromethyl-(1H)-1,2,4-triazole-3-carboxylate (S1-7), and related compounds, as are described in EP-A-174 562 and EP-A-346 620;

S1$^e$) compounds of the 5-benzyl- or 5-phenyl-2-isoxazoline-3-carboxylic acid type, or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds, as are described in WO-A-91/08202, or 5,5-diphenyl-2-isoxazolinecarboxylic acid (S1-10) or ethyl 5,5-diphenyl-2-isoxazolinecarboxylate (S1-11) ("isoxadifenethyl") or n-propyl 5,5-diphenyl-2-isoxazolinecarboxylate (S1-12) or of the ethyl 5-(4-fluorophenyl)-5-phenyl-2-isoxazoline-3-carboxylate type (S1-13), as described in the patent application WO-A-95/07897.

S2) Compounds from the group of 8-quinolinyloxy derivatives (S2):

S2$^a$) compounds of the 8-quinolinoxyacetic acid type (S2$^a$), preferably 1-methylhexyl (5-chloro-8-quinolinoxy)acetate ("cloquintocet-mexyl") (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as are described in EP-A-86 750, EP-A-94 349 and EP-A-191 736 or EP-A-0 492 366, and also (5-chloro-8-quinolinoxy)acetic acid (S2-10), its hydrates and salts, for example its lithium, sodium, potassium, calcium, magnesium, aluminum, iron, ammonium, quaternary ammonium, sulfonium or phosphonium salts, as are described in WO-A-2002/34048;

S2$^b$) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methylethyl (5-chloro-8-quinolinoxy)malonate and related compounds, as are described in EP-A-0 582 198.

S3) Active ingredients of the dichloroacetamide type (S3), which are often used as pre-emergence safeners (soil-active safeners), such as, for example, "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-diethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl] dichloroacetamide) from PPG Industries (S3-5), "DKA-24" (N-allyl-N-[(allylaminocarbonyl)methyl] dichloroacetamide) from Sagro-Chem (S3-6), "AD-67" or "MON 4660" (3-dichloroacetyl-1-oxa-3-azaspiro[4.5]decane) from Nitrokemia or Monsanto (S3-7), "TI-35" (1-dichloroacetylazepane) from TRI-Chemical RT (S3-8), "diclonon" (dicyclonone) or "BAS145138" or "LAB145138" (S3-9)

(3-dichloroacetyl-2,5,5-trimethyl-1,3-diazabicyclo[4.3.0] nonane) from BASF,

"Furilazol" or "MON 13900" ((RS)-3-dichloroacetyl-5-(2-fu 1)-2,2-dimethyl-oxazolidine) (S3-10), and also its (R)-isomer (S3-11).

S4) Compounds from the class of acylsulfonamides (S4):

S4$^a$) N-acylsulfonamides of the formula (S4$^a$) and salts thereof, as are described in WO-A-97/45016,

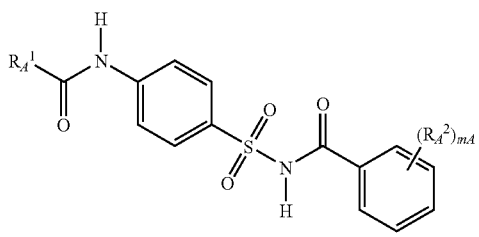

(S4$^a$)

in which
- $R_A^1$ is $(C_1\text{-}C_6)$alkyl which is substituted by $v_A$ substituents from the group halogen, $(C_1\text{-}C_4)$alkoxy, $(C_1\text{-}C_6)$haloalkoxy and $(C_1\text{-}C_4)$alkylthio and in the case of cyclic radicals also by $(C_1\text{-}C_4)$alkyl and $(C_1\text{-}C_4)$haloalkyl;
- $R_A^2$ is halogen, $(C_1\text{-}C_4)$alkyl, $(C_1\text{-}C_4)$alkoxy, $CF_3$;
- $m_A$ is 1 or 2;
- $v_A$ is 0, 1, 2 or 3;

S4$^b$) compounds of the 4-(benzoylsulfamoyl)benzamide type of the formula (S4$^b$) and salts thereof, as are described in WO-A-99/16744,

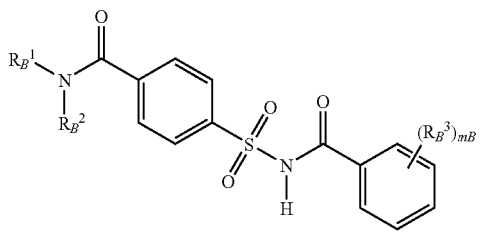

(S4$^b$)

in which
- $R_B^1$, $R_B^2$ independently of one another, are hydrogen, $(C_1\text{-}C_6)$alkyl, $(C_3\text{-}C_6)$alkenyl, $(C_3\text{-}C_6)$alkynyl,
- $R_B^3$ is halogen, $(C_1\text{-}C_4)$alkyl, $(C_1\text{-}C_4)$haloalkyl or $(C_1\text{-}C_4)$alkoxy and
- $m_B$ is 1 or 2, e.g. those in which
- $R_B^1$=cyclopropyl, $R_B^2$=hydrogen and $(R_B^3)$=2-OMe (S4-1, "cyprosulfamide"),
- $R_B^1$=cyclopropyl, $R_B^2$=hydrogen and $(R_B^3)$=5-Cl-2-OMe (S4-2),
- $R_B^1$=ethyl, $R_B^2$=hydrogen and $(R_8^3)$=2-OMe (S4-3),
- $R_B^1$=isopropyl, $R_B^2$=hydrogen and $(R_B^3)$=5-$C_{1\text{-}2}$-OMe (S4-4) and
- $R_B^1$=isopropyl, $R_B^2$=hydrogen and $(R_B^3)$=2-OMe (S4-5).

S4$^c$) Compounds from the class of benzoylsulfamoylphenylureas of the formula (S4$^c$), as are described in EP-A-365484

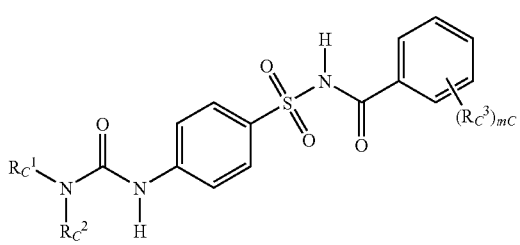

(S4$^c$)

in which
- $R_C^1$, $R_C^2$ independently of one another, are hydrogen, $(C_1\text{-}C_8)$alkyl, $(C_3\text{-}C_6)$alkenyl, $(C_3\text{-}C_6)$alkynyl,
- $R_C^3$ is halogen, $(C_1\text{-}C_4)$alkyl, $(C_1\text{-}C_4)$alkoxy, $CF_3$
- $m_C$ is 1 or 2;

for example
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea.

S5) Active ingredients from the class of hydroxyaromatics and aromatic-aliphatic carboxylic acid derivatives (S5), e.g.
ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 2-hydroxycinnamic acid, 2,4-dichlorocinnamic acid, as are described in WO-A-2004/084631, WO-A-2005/015994, WO-A-2005/016001.

S6) Active ingredients from the class of 1,2-dihydroquinoxalin-2-ones (S6), e.g. 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as are described in WO-A-2005/112630.

S7) Compounds from the class of diphenylmethoxyacetic acid derivatives (S7), e.g. methyl diphenylmethoxyacetate (CAS Reg. No. 41858-19-9) (S7-1), ethyl diphenylmethoxyacetate or diphenylmethoxyacetic acid, as are described in WO-A-98/38856.

S8) Compounds of the formula (S8), as are described in WO-A-98/27049

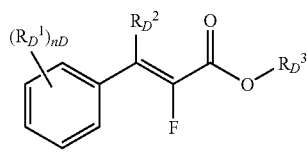

(S8)

in which the symbols and indices have the following meanings:
- $R_D^1$ is halogen, $(C_1\text{-}C_4)$alkyl, $(C_1\text{-}C_4)$haloalkyl, $(C_1\text{-}C_4)$alkoxy, $(C_1\text{-}C_4)$haloalkoxy,
- $R_D^2$ is hydrogen or $(C_1\text{-}C_4)$alkyl
- $R_{D3}$ is hydrogen, $(C_1\text{-}C_8)$alkyl, $(C_2\text{-}C_4)$alkenyl, $(C_2\text{-}C_4)$alkynyl, or aryl, where each of the aforementioned carbon-containing radicals is unsubstituted or substituted by one or more, preferably up to three, identical or different radicals from the group consisting of halogen and alkoxy; or salts thereof
- $n_D$ is an integer from 0 to 2.

S9) Active ingredients from the class of 3-(5-tetrazolylcarbonyl)-2-quinolones (S9), e.g. 1,2-dihydro-4-hydroxy-1-ethyl-3-(5-tetrazolylcarbonyl)-2-quinolone (CAS Reg. No. 219479-18-2), 1,2-dihydro-4-hydroxy-1-methyl-3-(5-tetrazolyl-carbonyl)-2-quinolone (CAS Reg. No. 95855-00-8), as described in WO-A-1999/000020.

S10) Compounds of the formulae (S10$^a$) or (S10$^b$)
as are described in WO-A-2007/023719 and WO-A-2007/023764

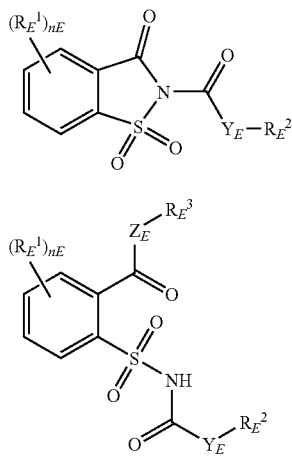

in which
$R_E^1$ is halogen, ($C_1$-$C_4$)alkyl, methoxy, nitro, cyano, $CF_3$, $OCF_3$
$Y_E$, $Z_E$ independently of one another, are O or S,
$n_E$ is an integer from 0 to 4,
$R_E^2$ is ($C_1$-$C_{16}$)alkyl, ($C_2$-$C_6$)alkenyl, aryl, benzyl, halobenzyl,
$R_E^3$ is hydrogen or ($C_1$-$C_6$)alkyl.

S11) Active ingredients of the oxyimino compound type (S11), which are known as seed dressings, such as, for example,
"oxabetrinil" ((Z)-1,3-dioxolan-2-ylmethoxyimino(phenyl)acetonitrile) (S11-1), which is known as seed dressing safener for barley against metolachlor damage,
"fluxofenim" (1-(4-chlorophenyl)-2,2,2-trifluoro-1-ethanone 0-(1,3-dioxolan-2-ylmethyl)oxime) (S11-2), which is known as seed dressing safener for barley against metolachlor damage, and
"cyometrinil" or "CGA-43089" ((Z)-cyanomethoxyimino (phenyl)acetonitrile) (S11-3), which is known as seed dressing safener for barley against metolachlor damage.

S12 Active ingredients from the class of isothiochromanones (S12), such as, for example, methyl [(3-oxo-1H-2-benzothiopyran-4(3H)ylidene)methoxy]acetate (CAS Reg. No. 205121-04-6) (S12-1) and related compounds from WO-A-1998/13361.

S13) One or more compounds from group (S13):
"naphthalic anhydride" (1,8-naphthalinedicarboxylic anhydride) (S13-1), which is known as seed dressing safener for corn against thiocarbamate herbicide damage,
"fenclorim" (4,6-dichloro-2-phenylpyrimidine) (S13-2), which is known as safener for pretilachlor in sown rice,
"flurazole" (benzyl-2-chloro-4-trifluoromethyl-1,3-thiazole-5-carboxylate) (S13-3), which is known as seed dressing safener for barley against alachlor and metolachlor damage,
"CL 304415" (CAS Reg. No. 31541-57-8)
(4-carboxy-3,4-dihydro-2H-1-benzopyran-4-acetic acid) (S13-4) from American Cyanamid, which is known as safener for corn against imidazolinone damage, "MG 191" (CAS Reg. No. 96420-72-3) (2-dichloromethyl-2-methyl-1,3-dioxolane) (S13-5) from Nitrokemia, which is known as safener for corn,
"MG-838" (CAS Reg. No. 133993-74-5)
(2-propenyl 1-oxa-4-azaspiro[4.5]decane-4-carbodithioate) (S13-6) from Nitrokemia
"disulfoton" (O,O-diethyl S-2-ethylthioethylphosphorodithioate) (S13-7),
"dietholate" (O,O-diethyl O-phenylphosphorothioate) (S13-8),
"mephenate" (4-chlorophenyl methylcarbamate) (S13-9).

S14) Active ingredients which, besides a herbicidal effect against harmful plants, also have a safener effect on crop plants such as rice, such as, for example,
"dimepiperate" or "MY-93" (S-1-methyl-1-phenylethyl piperidine-1-carbothioate), which is known as safener for rice against damage by the herbicide molinate,
"daimuron" or "SK 23" (1-(1-methyl-1-phenylethyl)-3-p-tolylurea), which is known as safener for rice against damage by the herbicide imazosulfuron,
"cumyluron"="JC-940" (3-(2-chlorophenylmethyl)-1-(1-methyl-1-phenylethyl)urea, see JP-A-60087254), which is known as safener for rice against damage by a number of herbicides,
"methoxyphenone" or "NK 049" (3,3'-dimethyl-4-methoxybenzophenone), which is known as safener for rice against damage by a number of herbicides,
"CSB" (1-bromo-4-(chloromethylsulfonyl)benzene) from Kumiai, (CAS Reg. No. 54091-06-4), which is known as safener against damage by a number of herbicides in rice.

S15) Active ingredients which are used primarily as herbicides, but also have safener effect on crop plants, e.g.
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichloro-ethyl).

Some of the safeners are also known as herbicides and thus, besides the herbicidal effect in respect of harmful plants, at the same time also develop a protective effect in the case of the crop plants.

The weight ratios of herbicide (mixture) to safener generally depends on the application rate of herbicide and the effectiveness of the particular safener and can vary within wide limits, for example in the range from 200:1 to 1:200, preferably 100:1 to 1:100, in particular 20:1 to 1:20. The safeners can be formulated analogously to the compounds according to the invention or mixtures thereof with further pesticides and are provided and applied as ready mix or tank mix with the compounds according to the invention.

For use, the formulations present in standard commercial form are optionally diluted in the customary manner, e.g. in the case of wettable powders, emulsifiable concentrates, dispersions and water-dispersible granules, by means of water. Dust-like preparations, soil and scattering granules, and sprayable solutions are usually not diluted more with further inert substances prior to application.

The required application rate of the compounds according to the invention varies with the external conditions such as temperature, humidity, the type of herbicide used, etc. It can vary within wide limits, e.g. between 0.001 and 10.0 kg/ha or more of active substance, but it is preferably between 0.005 and 5 kg/ha.

EXAMPLES

A. Synthesis Examples

Syntheses of compounds according to the invention are described below by way of example, without these examples having limiting character.

1. (6-Amino-5-chloro-2-(2,6-dichlorophenyl)pyrimidin-4-yl)propanedinitrile (Ex. No. 174)

Stage A:
   At 0° C., sodium hydride (45 mg as 60% strength suspension in mineral oil) is added to a solution of 72 mg of malonodinitrile in 10 ml of THF and the mixture is then stirred for 30 minutes at room temperature.
   4,5,6-Trichloro-2-(2,6-dichlorophenyl)pyrimidine (0.30 g; prepared analogously to the following procedure: K. Findeisen, K. Wagner, Synthesis 1978, 40-42) is added and the reaction mixture is stirred overnight at room temperature. The mixture is added to 10 ml of saturated ammonium chloride solution, extracted several times with ethyl acetate and the combined organic phases are washed with saturated sodium chloride solution. After drying over magnesium sulfate, the solvent is concentrated by evaporation under reduced pressure, giving compound No. 534.

Stage B:
   The resulting product is suspended in 5 ml of concentrated ammonia solution and reacted in a microwave device in a closed vessel for 8 hours at 150° C. The solution is then concentrated to half volume by evaporation under reduced pressure and acidified with 2N hydrochloric acid. The precipitated solid is washed with water and ethyl acetate and then dried. 0.19 g (61% of theory) of the desired product is obtained.

2. [6-Amino-5-chloro-2-phenylpyrimidin-4-yl]propanedinitrile (Ex. No. 1)
   The substance is synthesized analogously to the procedure for Ex. No. 174. The starting substance, 4,5,6-trichloro-2-phenylpyrimidine, is obtained in accordance with a method known in the literature: K. Findeisen, K. Wagner, Synthesis 1978, 40-42.

3. [6-Amino-5-chloro-2-(4-chlorophenyl)pyrimidin-4-yl] propanedinitrile (Ex. No. 29)
   The substance is synthesized analogously to the procedure for Ex. No. 174. The starting substance, 4,5,6-trichloro-2-(4-chlorophenyl)pyrimidine, is obtained by a method known in the literature: K. Findeisen, K. Wagner, Synthesis 1978, 40-42.

4. [5-Chloro-2-(4-chlorophenyl)-6-(methylamino)pyrimidin-4-yl]propanedinitrile (Ex. No. 41)
   The substance is obtained analogously to the procedure for Ex. No. 174. However, in stage B, methylamine (40% solution in MeOH) is used and the reaction is carried out in a microwave device at 120° C. for one hour.

5. [6-Amino-5-chloro-2-(3-fluorophenyl)pyrimidin-4-yl] propanedinitrile (Ex. No. 80)
   The substance is synthesized analogously to the procedure for Ex. No. 174. The starting substance, 4,5,6-trichloro-2-(3-fluorophenyl)pyrimidine, is obtained analogously to the method known in the literature: K. Findeisen, K. Wagner, Synthesis 1978, 40-42.

6. (6-Amino-5-chloro-2-methylpyrimidin-4-yl)propanedinitrile (Ex. No. 272)
   The substance is synthesized analogously to the procedure for Ex. No. 174. The starting substance, 4,5,6-trichloro-2-methylpyrimidine, is obtained according to a method known in the literature: H. Gershon, K. Dittmer, R. Braun, J. Org. Chem. 1961, 26, 1874-1877.

7. (6-Amino-5-chloro-2-tert-butylpyrimidin-4-yl)propanedinitrile (Ex. No. 277)
   The substance is synthesized analogously to the procedure for Ex. No. 174. The starting substance, 4,5,6-trichloro-2-tert-butylpyrimidine, is obtained analogously to the method known in the literature: H. Gershon, K. Dittmer, R. Braun, J. Org. Chem. 1961, 26, 1874-1877.

8. Ammonium [6-amino-5-chloro-2-(2,6-dichlorophenyl)pyrimidin-4-yl](dicyano)methanide (Ex. No. 371)
   100 mg of the compound from Ex. No. 174 are completely dissolved in ammonia solution (2M in EtOH, 2 ml), concentrated by evaporation under reduced pressure at 40° C. and the resulting solid is dried. 104 mg of the desired product are obtained.

9. Ammonium [6-amino-5-chloro-2-phenylpyrimidin-4-yl](dicyano)methanide (Ex. No. 288)
   The substance is synthesized analogously to the procedure for Ex. No. 371.

10. Sodium [6-amino-5-chloro-2-(4-chlorophenyl)pyrimidin-4-yl](dicyano)methanide (Ex. No. 304)
    By adding a stoichiometric amount of sodium methylate to the compound from Ex. No. 29 dissolved in ethanol, the corresponding sodium salt can be obtained after concentration by evaporation under reduced pressure and subsequent drying.

11. Ammonium [6-amino-5-chloro-2-(4-chlorophenyl)pyrimidin-4-yl](dicyano)methanide (Ex. No. 308)
    The substance is synthesized analogously to the procedure for Ex. No. 371.

12. Ammonium [6-amino-5-chloro-2-(3-fluorophenyl)pyrimidin-4-yl](dicyano)methanide (Ex. No. 332)
    The substance is synthesized analogously to the procedure for Ex. No. 371.

The compounds (Nos. 1-463) described in Tables 1-4 below are obtained analogously to the synthesis examples described above. The compounds (No. 464-585) described in Table 5 are obtained analogously to synthesis example A1, Stage A.

In Tables 1-5:

Me=methyl
Et=ethyl
cBu=cyclobutyl
cPr=cyclopropyl
iPr=isopropyl
cHex=cyclohexyl
tBu=tert-butyl
Ph=phenyl
Vin=vinyl
Ac=acetyl
Hal=halogen

TABLE 1

Compounds of the formula (I)

$$\text{structure: pyrimidine with } NR^3R^4 \text{ at 4-position, } R^2 \text{ at 5-position, } R^1 \text{ at 2-position, and } CH(CN)_2 \text{ at 6-position}$$

| Ex. No. | R¹ | R² | R³ | R⁴ |
|---|---|---|---|---|
| 1. | Ph | Cl | H | H |
| 2. | Ph | Br | H | H |
| 3. | Ph | Cl | H | Ac |
| 4. | Ph | Br | H | Ac |
| 5. | Ph | Cl | H | Me |
| 6. | Ph | Br | H | Me |
| 7. | 4-OMe—Ph | Cl | H | H |
| 8. | 4-OMe—Ph | Br | H | H |
| 9. | 4-NO₂—Ph | Cl | H | H |
| 10. | 4-NO₂—Ph | Br | H | H |
| 11. | 4-Me—Ph | F | H | H |
| 12. | 4-Me—Ph | Cl | H | H |
| 13. | 4-Me—Ph | Br | H | H |
| 14. | 4-I—Ph | Cl | H | H |
| 15. | 4-I—Ph | Br | H | H |
| 16. | 4-I—Ph | Cl | H | Ac |
| 17. | 4-I—Ph | Br | H | Ac |
| 18. | 4-I—Ph | Cl | H | Me |
| 19. | 4-I—Ph | Br | H | Me |
| 20. | 4-F—Ph | Cl | H | H |
| 21. | 4-F—Ph | Br | H | H |
| 22. | 4-F—Ph | Cl | H | Ac |
| 23. | 4-F—Ph | Br | H | Ac |
| 24. | 4-F—Ph | Cl | H | Me |
| 25. | 4-F—Ph | Br | H | Me |
| 26. | 4-COOMe—Ph | Cl | H | H |
| 27. | 4-COOMe—Ph | Br | H | H |
| 28. | 4-Cl—Ph | F | H | H |
| 29. | 4-Cl—Ph | Cl | H | H |
| 30. | 4-Cl—Ph | Br | H | H |
| 31. | 4-Cl—Ph | I | H | H |
| 32. | 4-Cl—Ph | CN | H | H |
| 33. | 4-Cl—Ph | NO₂ | H | H |
| 34. | 4-Cl—Ph | NO₂ | H | Me |
| 35. | 4-Cl—Ph | Cl | =CHN(Me)₂ | |
| 36. | 4-Cl—Ph | Br | =CHN(Me)₂ | |
| 37. | 4-Cl—Ph | Cl | H | Ac |
| 38. | 4-Cl—Ph | Br | H | Ac |
| 39. | 4-Cl—Ph | Cl | H | Et |
| 40. | 4-Cl—Ph | Br | H | Et |
| 41. | 4-Cl—Ph | Cl | H | Me |
| 42. | 4-Cl—Ph | Br | H | Me |
| 43. | 4-Cl—Ph | Cl | Me | Me |
| 44. | 4-Cl—Ph | Br | Me | Me |
| 45. | 4-CF₃—Ph | Cl | H | H |
| 46. | 4-CF₃—Ph | Br | H | H |
| 47. | 4-CF₃—Ph | Cl | H | Ac |
| 48. | 4-CF₃—Ph | Br | H | Ac |
| 49. | 4-CF₃—Ph | Cl | H | Me |
| 50. | 4-CF₃—Ph | Br | H | Me |
| 51. | 4-Br—Ph | F | H | H |
| 52. | 4-Br—Ph | Cl | H | H |
| 53. | 4-Br—Ph | Br | H | H |
| 54. | 4-Br—Ph | I | H | H |
| 55. | 4-Br—Ph | CN | H | H |
| 56. | 4-Br—Ph | NO₂ | H | H |
| 57. | 4-Br—Ph | Cl | =CHN(Me)₂ | |
| 58. | 4-Br—Ph | Br | =CHN(Me)₂ | |
| 59. | 4-Br—Ph | Cl | H | Ac |
| 60. | 4-Br—Ph | Br | H | Ac |
| 61. | 4-Br—Ph | Cl | H | Et |
| 62. | 4-Br—Ph | Br | H | Et |
| 63. | 4-Br—Ph | Cl | H | Me |
| 64. | 4-Br—Ph | Br | H | Me |
| 65. | 4-Br—Ph | Cl | Me | Me |
| 66. | 4-Br—Ph | Br | Me | Me |
| 67. | 3-OMe-4-F—Ph | F | H | H |
| 68. | 3-OMe-4-F—Ph | Cl | H | H |
| 69. | 3-OMe-4-F—Ph | Br | H | H |
| 70. | 3-OMe-4-Cl—Ph | F | H | H |
| 71. | 3-OMe-4-Cl—Ph | Cl | H | H |
| 72. | 3-OMe-4-Cl—Ph | Br | H | H |
| 73. | 3-Me—Ph | Cl | H | H |
| 74. | 3-Me—Ph | Br | H | H |
| 75. | 3-Me—Ph | F | H | H |
| 76. | 3-Me-4-Cl—Ph | F | H | H |
| 77. | 3-Me-4-Cl—Ph | Cl | H | H |
| 78. | 3-Me-4-Cl—Ph | Br | H | H |
| 79. | 3-F—Ph | F | H | H |
| 80. | 3-F—Ph | Cl | H | H |
| 81. | 3-F—Ph | Br | H | H |
| 82. | 3-Cl—Ph | Cl | H | H |
| 83. | 3-Cl—Ph | Br | H | H |
| 84. | 3-CF₃—Ph | F | H | H |
| 85. | 3-CF₃—Ph | Cl | H | H |
| 86. | 3-CF₃—Ph | Br | H | H |
| 87. | 3-CF₃-4-Cl—Ph | Cl | H | H |
| 88. | 3-CF₃-4-Cl—Ph | Br | H | H |
| 89. | 3-CF₃-4-Cl—Ph | F | H | H |
| 90. | 3-CF₃-4-Cl—Ph | I | H | H |
| 91. | 3,6-di-Cl—Ph | F | H | H |
| 92. | 3,6-di-Cl—Ph | Cl | H | H |
| 93. | 3,6-di-Cl—Ph | Br | H | H |
| 94. | 3,5-di-Cl—Ph | F | H | H |
| 95. | 3,5-di-Cl—Ph | Cl | H | H |
| 96. | 3,5-di-Cl—Ph | Br | H | H |
| 97. | 3,5-di-CF₃—Ph | F | H | H |
| 98. | 3,5-di-CF₃—Ph | Cl | H | H |
| 99. | 3,5-di-CF₃—Ph | Br | H | H |
| 100. | 3,4-di-OMe—Ph | F | H | H |
| 101. | 3,4-di-OMe—Ph | Cl | H | H |
| 102. | 3,4-di-OMe—Ph | Br | H | H |
| 103. | 3,4-di-Cl—Ph | F | H | H |
| 104. | 3,4-di-Cl—Ph | Cl | H | H |
| 105. | 3,4-di-Cl—Ph | Br | H | H |
| 106. | 2-F-6-Cl—Ph | F | H | H |
| 107. | 2-F-6-Cl—Ph | Cl | H | H |
| 108. | 2-F-6-Cl—Ph | Br | H | H |
| 109. | 2-F-4-Cl—Ph | F | H | H |
| 110. | 2-F-4-Cl—Ph | Cl | H | H |
| 111. | 2-F-4-Cl—Ph | Br | H | H |
| 112. | 2-F-4-Cl-5-OMe—Ph | Cl | H | H |
| 113. | 2-F-4-Cl-5-OMe—Ph | Br | H | H |
| 114. | 2-F-4-Cl-5-OMe—Ph | Cl | H | Ac |
| 115. | 2-F-4-Cl-5-OMe—Ph | Br | H | Ac |
| 116. | 2-F-4-Cl-5-OMe—Ph | Cl | H | Me |
| 117. | 2-F-4-Cl-5-OMe—Ph | Br | H | Me |
| 118. | 2-F-4,5-di-Cl—Ph | F | H | H |
| 119. | 2-F-4,5-di-Cl—Ph | Cl | H | H |
| 120. | 2-F-4,5-di-Cl—Ph | Br | H | H |
| 121. | 2-F-3-SMe-4-Cl—Ph | Cl | H | H |
| 122. | 2-F-3-SMe-4-Cl—Ph | Br | H | H |
| 123. | 2-F-3-SMe-4-Cl—Ph | Cl | H | Ac |
| 124. | 2-F-3-SMe-4-Cl—Ph | Br | H | Ac |
| 125. | 2-F-3-SMe-4-Cl—Ph | Cl | H | Me |
| 126. | 2-F-3-SMe-4-Cl—Ph | Br | H | Me |
| 127. | 2-F-3-SCF₃-4-Cl—Ph | F | H | H |
| 128. | 2-F-3-SCF₃-4-Cl—Ph | Cl | H | H |
| 129. | 2-F-3-SCF₃-4-Cl—Ph | Br | H | H |
| 130. | 2-F-3-S(O₂)Me-4-Cl—Ph | F | H | H |
| 131. | 2-F-3-S(O₂)Me-4-Cl—Ph | Cl | H | H |
| 132. | 2-F-3-S(O₂)Me-4-Cl—Ph | Br | H | H |
| 133. | 2-F-3-S(O)Me-4-Cl—Ph | F | H | H |
| 134. | 2-F-3-S(O)Me-4-Cl—Ph | Cl | H | H |

TABLE 1-continued

Compounds of the formula (I)

(I)

$$\text{Structure: Pyrimidine with } NR^3R^4 \text{ at 4-position, } R^2 \text{ at 5-position, } R^1 \text{ at 2-position, } CH(CN)_2 \text{ at 6-position}$$

| Ex. No. | R¹ | R² | R³ | R⁴ |
|---|---|---|---|---|
| 135. | 2-F-3-S(O)Me-4-Cl—Ph | Br | H | H |
| 136. | 2-F-3-OMe-4-Cl—Ph | F | H | H |
| 137. | 2-F-3-OMe-4-Cl—Ph | Cl | H | H |
| 138. | 2-F-3-OMe-4-Cl—Ph | Br | H | H |
| 139. | 2-F-3-OMe-4-Cl—Ph | I | H | H |
| 140. | 2-F-3-OMe-4-Cl—Ph | CN | H | H |
| 141. | 2-F-3-OMe-4-Cl—Ph | NO₂ | H | H |
| 142. | 2-F-3-OMe-4-Cl—Ph | Cl | =CHN(Me)₂ | |
| 143. | 2-F-3-OMe-4-Cl—Ph | Br | =CHN(Me)₂ | |
| 144. | 2-F-3-OMe-4-Cl—Ph | Cl | H | Ac |
| 145. | 2-F-3-OMe-4-Cl—Ph | Br | H | Ac |
| 146. | 2-F-3-OMe-4-Cl—Ph | Cl | H | Et |
| 147. | 2-F-3-OMe-4-Cl—Ph | Br | H | Et |
| 148. | 2-F-3-OMe-4-Cl—Ph | Cl | H | Me |
| 149. | 2-F-3-OMe-4-Cl—Ph | Br | H | Me |
| 150. | 2-F-3-OMe-4-Cl—Ph | Cl | Me | Me |
| 151. | 2-F-3-OMe-4-Cl—Ph | Br | Me | Me |
| 152. | 2-F-3-OEt-4-Cl—Ph | Cl | H | H |
| 153. | 2-F-3-OEt-4-Cl—Ph | Br | H | H |
| 154. | 2-F-3-OEt-4-Cl—Ph | Cl | H | Ac |
| 155. | 2-F-3-OEt-4-Cl—Ph | Br | H | Ac |
| 156. | 2-F-3-OEt-4-Cl—Ph | Cl | H | Me |
| 157. | 2-F-3-OEt-4-Cl—Ph | Br | H | Me |
| 158. | 2-F-3-OCF₃-4-Cl—Ph | F | H | H |
| 159. | 2-F-3-OCF₃-4-Cl—Ph | Cl | H | H |
| 160. | 2-F-3-OCF₃-4-Cl—Ph | Br | H | H |
| 161. | 2-F-3-NMe₂-4-Cl—Ph | F | H | H |
| 162. | 2-F-3-NMe₂-4-Cl—Ph | Cl | H | H |
| 163. | 2-F-3-NMe₂-4-Cl—Ph | Br | H | H |
| 164. | 2-F-3-Me-4-Cl—Ph | F | H | H |
| 165. | 2-F-3-Me-4-Cl—Ph | Cl | H | H |
| 166. | 2-F-3-Me-4-Cl—Ph | Br | H | H |
| 167. | 2-Cl—Ph | F | H | H |
| 168. | 2-Cl—Ph | Cl | H | H |
| 169. | 2-Cl—Ph | Br | H | H |
| 170. | 2,6-di-F-3-OMe-4-Cl—Ph | F | H | H |
| 171. | 2,6-di-F-3-OMe-4-Cl—Ph | Cl | H | H |
| 172. | 2,6-di-F-3-OMe-4-Cl—Ph | Br | H | H |
| 173. | 2,6-di-Cl—Ph | F | H | H |
| 174. | 2,6-di-Cl—Ph | Cl | H | H |
| 175. | 2,6-di-Cl—Ph | Br | H | H |
| 176. | 2,5-di-Cl—Ph | F | H | H |
| 177. | 2,5-di-Cl—Ph | Cl | H | H |
| 178. | 2,5-di-Cl—Ph | Br | H | H |
| 179. | 2,4-di-F-5-OMe—Ph | F | H | H |
| 180. | 2,4-di-F-5-OMe—Ph | Cl | H | H |
| 181. | 2,4-di-F-5-OMe—Ph | Br | H | H |
| 182. | 2,4-di-F-3-OMe—Ph | F | H | H |
| 183. | 2,4-di-F-3-OMe—Ph | Cl | H | H |
| 184. | 2,4-di-F-3-OMe—Ph | Br | H | H |
| 185. | 2,4-di-Cl—Ph | F | H | H |
| 186. | 2,4-di-Cl—Ph | Cl | H | H |
| 187. | 2,4-di-Cl—Ph | Br | H | H |
| 188. | 2,4-di-Cl—Ph | F | H | Ac |
| 189. | 2,4-di-Cl—Ph | Cl | H | Ac |
| 190. | 2,4-di-Cl—Ph | Br | H | Ac |
| 191. | 2,4-di-Cl-5-F—Ph | F | H | H |
| 192. | 2,4-di-Cl-5-F—Ph | Cl | H | H |
| 193. | 2,4-di-Cl-5-F—Ph | Br | H | H |
| 194. | 2,4-di-Cl-3-OMe—Ph | F | H | H |
| 195. | 2,4-di-Cl-3-OMe—Ph | Cl | H | H |
| 196. | 2,4-di-Cl-3-OMe—Ph | Br | H | H |
| 197. | 2,4,6-tri-Cl—Ph | F | H | H |
| 198. | 2,4,6-tri-Cl—Ph | Cl | H | H |
| 199. | 2,4,6-tri-Cl—Ph | Br | H | H |
| 200. | 2,4-di-Me—Ph | Cl | H | H |
| 201. | 2,4-di-F—Ph | Cl | H | H |
| 202. | 2,3-di-F-4-Me—Ph | Cl | H | H |
| 203. | 2-NH₂-5-F—Ph | Cl | H | H |
| 204. | 3-F-4-Me—Ph | Cl | H | H |
| 205. | 3-Me-4-F—Ph | Cl | H | H |
| 206. | 3-NO₂—Ph | Cl | H | H |
| 207. | 2,3-di-Cl—Ph | Cl | H | H |
| 208. | 2-F-4-Br—Ph | Cl | H | H |
| 209. | 2-F-4-Me—Ph | Cl | H | H |
| 210. | 3,5-di-F-4-Cl—Ph | Cl | H | H |

TABLE 2

Compounds of the formula (I)

(I)

| Ex. No. | R¹ | R² | R³ | R⁴ |
|---|---|---|---|---|
| 211. | 1-Cl—cPr | F | H | H |
| 212. | 1-Cl—cPr | Cl | H | H |
| 213. | 1-Cl—cPr | Br | H | H |
| 214. | 1-Cl—cPr | Cl | H | Ac |
| 215. | 1-Cl—cPr | Br | H | Ac |
| 216. | 1-Cl—cPr | Cl | H | Me |
| 217. | 1-Cl—cPr | Br | H | Me |
| 218. | 2-cPr—Vin | Cl | H | H |
| 219. | 2-cPr—Vin | Br | H | H |
| 220. | 2-di-Me—cPr | F | H | H |
| 221. | 2-di-Me—cPr | Cl | H | H |
| 222. | 2-di-Me—cPr | Br | H | H |
| 223. | 2-di-Me—cPr | Cl | H | Ac |
| 224. | 2-di-Me—cPr | Br | H | Ac |
| 225. | 2-di-Me—cPr | Cl | H | Me |
| 226. | 2-di-Me—cPr | Br | H | Me |
| 227. | 2-Me—Vin | Cl | H | H |
| 228. | 2-Me—Vin | Br | H | H |
| 229. | 2-Ph—Vin | Cl | H | H |
| 230. | 2-Ph—Vin | Br | H | H |
| 231. | 4-Cl—PhCH₂ | Cl | H | H |
| 232. | 4-Cl—PhCH₂ | Br | H | H |
| 233. | cBu | F | H | H |
| 234. | cBu | Cl | H | H |
| 235. | cBu | Br | H | H |
| 236. | CF₃ | F | H | H |
| 237. | CF₃ | Cl | H | H |
| 238. | CF₃ | Br | H | H |
| 239. | cHex | F | H | H |
| 240. | cHex | Cl | H | H |
| 241. | cHex | Br | H | H |
| 242. | cHex | Cl | H | Ac |
| 243. | cHex | Br | H | Ac |
| 244. | cHex | Cl | H | Me |
| 245. | cHex | Br | H | Me |
| 246. | cPr | Cl | =CHN(Me)₂ | |
| 247. | cPr | Br | =CHN(Me)₂ | |
| 248. | cPr | F | H | H |
| 249. | cPr | Cl | H | H |
| 250. | cPr | Br | H | H |
| 251. | cPr | I | H | H |

TABLE 2-continued

Compounds of the formula (I)

(I) Structure: pyrimidine with NR³R⁴ at 6-position, R² at 5-position, R¹ at 2-position, CH(CN)₂ at 4-position.

| Ex. No. | R¹ | R² | R³ | R⁴ |
|---|---|---|---|---|
| 252. | cPr | CN | H | H |
| 253. | cPr | NO₂ | H | H |
| 254. | cPr | Cl | H | Ac |
| 255. | cPr | Br | H | Ac |
| 256. | cPr | Cl | H | Et |
| 257. | cPr | Br | H | Et |
| 258. | cPr | Cl | H | Me |
| 259. | cPr | Br | H | Me |
| 260. | cPr | Cl | Me | Me |
| 261. | cPr | Br | Me | Me |
| 262. | Hex | Cl | H | H |
| 263. | Hex | Br | H | H |
| 264. | iPr | F | H | H |
| 265. | iPr | Cl | H | H |
| 266. | iPr | Br | H | H |
| 267. | iPr | I | H | H |
| 268. | iPr | Cl | H | Ac |
| 269. | iPr | Br | H | Ac |
| 270. | iPr | Cl | H | Me |
| 271. | iPr | Br | H | Me |
| 272. | Me | Cl | H | H |
| 273. | Me | Br | H | H |
| 274. | PhCH₂ | Cl | H | H |
| 275. | PhCH₂ | Br | H | H |
| 276. | tBu | F | H | H |
| 277. | tBu | Cl | H | H |
| 278. | tBu | Br | H | H |
| 279. | tBu | I | H | H |
| 280. | Vin | F | H | H |
| 281. | Vin | Cl | H | H |
| 282. | Vin | Br | H | H |

TABLE 3

Salts of the compounds of the formula (I)

| Ex. No. | R¹ | R² | R³ | R⁴ | M# |
|---|---|---|---|---|---|
| 283. | Ph | Cl | H | H | Li⁺ |
| 284. | Ph | Cl | H | H | Na⁺ |
| 285. | Ph | Cl | H | H | K⁺ |
| 286. | Ph | Cl | H | H | Ca²⁺ |
| 287. | Ph | Cl | H | H | Mg²⁺ |
| 288. | Ph | Cl | H | H | NH₄⁺ |
| 289. | Ph | Cl | H | H | NH₃Me⁺ |
| 290. | Ph | Cl | H | H | NH₂Me₂⁺ |
| 291. | Ph | Cl | H | H | NHMe₃⁺ |
| 292. | Ph | Cl | H | H | NMe₄⁺ |
| 293. | Ph | Br | H | H | NH₄⁺ |
| 294. | 4-OMe—Ph | Cl | H | H | NH₄⁺ |
| 295. | 4-NO₂—Ph | Cl | H | H | NH₄⁺ |
| 296. | 4-Me—Ph | Cl | H | H | NH₄⁺ |
| 297. | 4-I—Ph | Cl | H | H | NH₄⁺ |
| 298. | 4-F—Ph | Cl | H | H | Na⁺ |
| 299. | 4-F—Ph | Cl | H | H | K⁺ |
| 300. | 4-F—Ph | Cl | H | H | NH₄⁺ |
| 301. | 4-F—Ph | Cl | H | Ac | NH₄⁺ |
| 302. | 4-F—Ph | Cl | H | Me | NH₄⁺ |
| 303. | 4-Cl—Ph | Cl | H | H | Li⁺ |
| 304. | 4-Cl—Ph | Cl | H | H | Na⁺ |
| 305. | 4-Cl—Ph | Cl | H | H | K⁺ |
| 306. | 4-Cl—Ph | Cl | H | H | Ca²⁺ |
| 307. | 4-Cl—Ph | Cl | H | H | Mg²⁺ |
| 308. | 4-Cl—Ph | Cl | H | H | NH₄⁺ |
| 309. | 4-Cl—Ph | Cl | H | H | NH₃Me⁺ |
| 310. | 4-Cl—Ph | Cl | H | H | NH₂Me₂⁺ |
| 311. | 4-Cl—Ph | Cl | H | H | NHMe₃⁺ |
| 312. | 4-Cl—Ph | Cl | H | H | NMe₄⁺ |
| 313. | 4-Cl—Ph | Br | H | H | NH₄⁺ |
| 314. | 4-Cl—Ph | Cl | H | Ac | NH₄⁺ |
| 315. | 4-Cl—Ph | Cl | H | Et | NH₄⁺ |
| 316. | 4-Cl—Ph | Cl | H | Me | NH₄⁺ |
| 317. | 4-Cl—Ph | Cl | Me | Me | NH₄⁺ |
| 318. | 4-CF₃—Ph | Cl | H | H | NH₄⁺ |
| 319. | 4-Br—Ph | Cl | H | H | Na⁺ |
| 320. | 4-Br—Ph | Cl | H | H | K⁺ |
| 321. | 4-Br—Ph | Cl | H | H | NH₄⁺ |
| 322. | 4-Br—Ph | Br | H | H | Na⁺ |
| 323. | 4-Br—Ph | Br | H | H | K⁺ |
| 324. | 4-Br—Ph | Br | H | H | NH₄⁺ |
| 325. | 4-Br—Ph | Cl | H | Ac | NH₄⁺ |
| 326. | 4-Br—Ph | Cl | H | Et | NH₄⁺ |
| 327. | 4-Br—Ph | Cl | H | Me | NH₄⁺ |
| 328. | 3-OMe-4-F—Ph | Cl | H | H | Na⁺ |
| 329. | 3-OMe-4-F—Ph | Cl | H | H | NH₄⁺ |
| 330. | 3-Me—Ph | Cl | H | H | NH₄⁺ |
| 331. | 3-Me-4-Cl—Ph | Cl | H | H | NH₄⁺ |
| 332. | 3-F—Ph | Cl | H | H | NH₄⁺ |
| 333. | 3-Cl—Ph | Cl | H | H | NH₄⁺ |
| 334. | 3-CF₃—Ph | Cl | H | H | NH₄⁺ |
| 335. | 3-CF₃-4-Cl—Ph | Cl | H | H | NH₄⁺ |
| 336. | 3,6-di-Cl—Ph | Cl | H | H | NH₄⁺ |
| 337. | 3,5-di-Cl—Ph | Cl | H | H | NH₄⁺ |
| 338. | 3,5-di-CF₃—Ph | Cl | H | H | NH₄⁺ |
| 339. | 3,4-di-OMe—Ph | Cl | H | H | NH₄⁺ |
| 340. | 3,4-di-Cl—Ph | Cl | H | H | Na⁺ |
| 341. | 3,4-di-Cl—Ph | Cl | H | H | NH₄⁺ |
| 342. | 2-F-6-Cl—Ph | Cl | H | H | NH₄⁺ |
| 343. | 2-F-4-Cl—Ph | Cl | H | H | Na⁺ |
| 344. | 2-F-4-Cl—Ph | Cl | H | H | K⁺ |
| 345. | 2-F-4-Cl—Ph | Cl | H | H | NH₄⁺ |
| 346. | 2-F-4-Cl-5-OMe—Ph | Cl | H | H | Na⁺ |
| 347. | 2-F-4-Cl-5-OMe—Ph | Cl | H | H | NH₄⁺ |
| 348. | 2-F-4-Cl-5-OMe—Ph | Cl | H | Ac | NH₄⁺ |
| 349. | 2-F-4,5-di-Cl—Ph | Cl | H | H | NH₄⁺ |
| 350. | 2-F-3-SMe-4-Cl—Ph | Cl | H | H | NH₄⁺ |
| 351. | 2-F-3-SCF₃-4-Cl—Ph | Cl | H | H | NH₄⁺ |
| 352. | 2-F-3-S(O₂)Me-4-Cl—Ph | Cl | H | H | NH₄⁺ |
| 353. | 2-F-3-S(O)Me-4-Cl—Ph | Cl | H | H | NH₄⁺ |
| 354. | 2-F-3-OMe-4-Cl—Ph | Cl | H | H | Li⁺ |
| 355. | 2-F-3-OMe-4-Cl—Ph | Cl | H | H | Na⁺ |
| 356. | 2-F-3-OMe-4-Cl—Ph | Cl | H | H | K⁺ |
| 357. | 2-F-3-OMe-4-Cl—Ph | Cl | H | H | Ca²⁺ |
| 358. | 2-F-3-OMe-4-Cl—Ph | Cl | H | H | Mg²⁺ |
| 359. | 2-F-3-OMe-4-Cl—Ph | Cl | H | H | NH₄⁺ |
| 360. | 2-F-3-OMe-4-Cl—Ph | Cl | H | H | NH₃Me⁺ |
| 361. | 2-F-3-OMe-4-Cl—Ph | Cl | H | H | NH₂Me₂⁺ |
| 362. | 2-F-3-OMe-4-Cl—Ph | Cl | H | H | NHMe₃⁺ |
| 363. | 2-F-3-OMe-4-Cl—Ph | Cl | H | H | NMe₄⁺ |
| 364. | 2-F-3-OMe-4-Cl—Ph | Cl | H | Ac | NH₄⁺ |
| 365. | 2-F-3-OMe-4-Cl—Ph | Cl | H | Me | NH₄⁺ |
| 366. | 2-F-3-OEt-4-Cl—Ph | Cl | H | H | NH₄⁺ |
| 367. | 2-F-3-OCF₃-4-Cl—Ph | Cl | H | H | NH₄⁺ |
| 368. | 2-F-3-NMe₂-4-Cl—Ph | Cl | H | H | NH₄⁺ |

TABLE 3-continued

Salts of the compounds of the formula (I)

(I) Structure: 4-NR³R⁴, 5-R², 2-R¹, 6-C(CN)₂M pyrimidine

| Ex. No. | R¹ | R² | R³ | R⁴ | M# |
|---|---|---|---|---|---|
| 369. | 2-Cl—Ph | Cl | H | H | NH₄⁺ |
| 370. | 2,6-di-F-3-OMe-4-Cl—Ph | Cl | H | H | NH₄⁺ |
| 371. | 2,6-di-Cl—Ph | Cl | H | H | NH₄⁺ |
| 372. | 2,5-di-Cl—Ph | Cl | H | H | NH₄⁺ |
| 373. | 2 4-di-F-5-OMe—Ph | Cl | H | H | NH₄⁺ |
| 374. | 2,4-di-F-3-OMe—Ph | Cl | H | H | NH₄⁺ |
| 375. | 2,4-di-Cl—Ph | Cl | H | H | NH₄⁺ |
| 376. | 2,4-di-Cl—Ph | Cl | H | H | NH₄⁺ |
| 377. | 2,4-di-Cl-5-F—Ph | Cl | H | H | NH₄⁺ |
| 378. | 2,4-di-Cl-3-OMe—Ph | Cl | H | H | NH₄⁺ |
| 379. | 2,4,6-tri-Cl—Ph | Cl | H | H | NH₄⁺ |
| 380. | 2,3-di-Cl—Ph | Cl | H | H | Na⁺ |
| 381. | 4-COOH—Ph | Cl | H | H | NH₄⁺ |
| 382. | 2-F-4-Br—Ph | Cl | H | H | NH₄⁺ |
| 383. | 2,4-di-F—Ph | Cl | H | H | NH₄⁺ |
| 384. | 4-Cl—Ph | NO₂ | H | H | NH₄⁺ |
| 385. | 3-F-4-Me—Ph | Cl | H | H | NH₄⁺ |
| 386. | 3,5-di-F-4-Cl—Ph | Cl | H | H | NH₄⁺ |
| 387. | 2,3-di-F-4-Me—Ph | Cl | H | H | NH₄⁺ |
| 388. | 2,4-di-Me—Ph | Cl | H | H | NH₄⁺ |
| 389. | 3-Me-4-F—Ph | Cl | H | H | NH₄⁺ |
| 390. | 2,3-di-Cl—Ph | Cl | H | H | NH₄⁺ |
| 391. | 2-F-4-Me—Ph | Cl | H | H | NH₄⁺ |
| 392. | 2-F-4-Br—Ph | Cl | H | H | NH₄⁺ |
| 393. | 4-Cl—Ph | Cl | Me | Me | Na⁺ |

TABLE 4

Salts of the compounds of the formula (I)

| Ex. No. | R¹ | R² | R³ | R⁴ | M# |
|---|---|---|---|---|---|
| 394. | 1-Cl—cPr | F | H | H | NH₄⁺ |
| 395. | 1-Cl—cPr | Cl | H | H | Li⁺ |
| 396. | 1-Cl—cPr | Cl | H | H | Na⁺ |
| 397. | 1-Cl—cPr | Cl | H | H | K⁺ |
| 398. | 1-Cl—cPr | Cl | H | H | Ca²⁺ |
| 399. | 1-Cl—cPr | Cl | H | H | Mg²⁺ |
| 400. | 1-Cl—cPr | Cl | H | H | NH₄⁺ |
| 401. | 1-Cl—cPr | Cl | H | H | NH₃Me⁺ |
| 402. | 1-Cl—cPr | Cl | H | H | NH₂Me₂⁺ |
| 403. | 1-Cl—cPr | Cl | H | H | NHMe₃⁺ |
| 404. | 1-Cl—cPr | Cl | H | H | NMe₄⁺ |
| 405. | 1-Cl—cPr | Br | H | H | Na⁺ |
| 406. | 1-Cl—cPr | Br | H | H | NH₄⁺ |
| 407. | 1-Cl—cPr | Cl | H | Me | NH₄⁺ |
| 408. | 1-Cl—cPr | Br | H | Me | NH₄⁺ |
| 409. | 2-cPr—Vin | Cl | H | H | NH₄⁺ |
| 410. | 2-di-Me—cPr | Cl | H | H | Li⁺ |
| 411. | 2-di-Me—cPr | Cl | H | H | Na⁺ |
| 412. | 2-di-Me—cPr | Cl | H | H | K⁺ |
| 413. | 2-di-Me—cPr | Cl | H | H | Ca²⁺ |
| 414. | 2-di-Me—cPr | Cl | H | H | Mg²⁺ |
| 415. | 2-di-Me—cPr | Cl | H | H | NH₄⁺ |
| 416. | 2-di-Me—cPr | Cl | H | H | NH₃Me⁺ |
| 417. | 2-di-Me—cPr | Cl | H | H | NH₂Me₂⁺ |
| 418. | 2-di-Me—cPr | Cl | H | H | NHMe₃⁺ |

TABLE 4-continued

Salts of the compounds of the formula (I)

| Ex. No. | R¹ | R² | R³ | R⁴ | M# |
|---|---|---|---|---|---|
| 419. | 2-di-Me—cPr | Cl | H | H | NMe₄⁺ |
| 420. | 2-di-Me—cPr | Br | H | H | NH₄⁺ |
| 421. | 2-Me—Vin | Cl | H | H | NH₄⁺ |
| 422. | 2-Ph—Vin | Cl | H | H | NH₄⁺ |
| 423. | 4-Cl—PhCH₂ | Cl | H | H | Na⁺ |
| 424. | 4-Cl—PhCH₂ | Cl | H | H | NH₄⁺ |
| 425. | cBu | Cl | H | H | Na⁺ |
| 426. | cBu | Cl | H | H | NH₄⁺ |
| 427. | cBu | Br | H | H | Na⁺ |
| 428. | cBu | Br | H | H | NH₄⁺ |
| 429. | CF₃ | Cl | H | H | NH₄⁺ |
| 430. | cHex | Cl | H | H | NH₄⁺ |
| 431. | cPr | F | H | H | NH₄⁺ |
| 432. | cPr | Cl | H | H | Li⁺ |
| 433. | cPr | Cl | H | H | Na⁺ |
| 434. | cPr | Cl | H | H | K⁺ |
| 435. | cPr | Cl | H | H | Ca²⁺ |
| 436. | cPr | Cl | H | H | Mg²⁺ |
| 437. | cPr | Cl | H | H | NH₄⁺ |
| 438. | cPr | Cl | H | H | NH₃Me⁺ |
| 439. | cPr | Cl | H | H | NH₂Me₂⁺ |
| 440. | cPr | Cl | H | H | NHMe₃⁺ |
| 441. | cPr | Cl | H | H | NMe₄⁺ |
| 442. | cPr | Br | H | H | Na⁺ |
| 443. | cPr | Br | H | H | NH₄⁺ |
| 444. | cPr | Cl | H | Ac | Na⁺ |
| 445. | cPr | Cl | H | Ac | NH₄⁺ |
| 446. | cPr | Cl | H | Me | NH₄⁺ |
| 447. | cPr | Cl | Me | Me | NH₄⁺ |
| 448. | Hex | Cl | H | H | NH₄⁺ |
| 449. | iPr | Cl | H | H | Na⁺ |
| 450. | iPr | Cl | H | H | NH₄⁺ |
| 451. | iPr | Br | H | H | NH₄⁺ |
| 452. | Me | Cl | H | H | NH₄⁺ |
| 453. | PhCH₂ | Cl | H | H | NH₄⁺ |
| 454. | PhCH₂ | Cl | H | H | Na⁺ |
| 455. | tBu | Cl | H | H | NH₄⁺ |
| 456. | tBu | Br | H | H | NH₄⁺ |
| 457. | Vin | Cl | H | H | Na⁺ |
| 458. | Vin | Cl | H | H | NH₄⁺ |
| 459. | Vin | Br | H | H | NH₄⁺ |
| 460. | cPr | NO₂ | H | H | NH₄⁺ |
| 461. | tBu | Br | H | H | Na⁺ |
| 462. | cHex | Cl | H | H | Na⁺ |
| 463. | CF₃ | F | H | H | NH₄⁺ |

Physical data of selected compounds from Tables 1-4:

| Ex. No. | Data |
|---|---|
| 1. | 7.99 (m, 2H), 7.62 (m, 3H), 7.40 (bs, 2H) |
| 9. | 8.41 (d, 2H), 8.28 (d, 2H), 7.16 (bs, 2H) |
| 12. | 7.91 (d, 2H), 7.41 (d, 2H), 7.38 (bs, 2H), 2.40 (s, 3H) |
| 20. | 8.05 (dd, 2H), 7.46 (dd, 2H), 7.32 (bs, 2H) |
| 29. | 8.00 (d, 2H), 7.70 (d, 2H), 7.40 (bs, 2H) |
| 33. | 8.22 (d, 2H), 7.87 (bs, 2H), 7.48 (d, 2H) |
| 41. | 8.08 (d, 2H), 7.60 (d, 2H), 4.40 (bs, 2H), 2.98 (s, 3H) |
| 43. | 8.18 (d, 2H), 7.54 (d, 2H), 3.08 (s, 6H) |
| 45. | 8.21 (d, 2H), 7.98 (d, 2H), 7.27 (bs, 2H) |
| 53. | 7.94 (d, 2H), 7.82 (d, 2H), 7.17 (bs, 2H) |
| 80. | 7.85 (m, 1H), 7.78 (m, 1H), 7.64 (m, 1H), 7.49 (m, 1H), 7.31 (bs, 2H) |
| 82. | 8.03 (s, 1H), 7.97 (d, 1H), 7.69 (d, 1H), 7.62 (t, 1H), 7.28 (bs, 2H) |

-continued

| Ex. No. | Data |
|---|---|
| 87. | 8.49 (s, 1H), 8.30 (d, 1H), 7.93 (d, 1H), 7.15 (bs, 2H) |
| 104. | 8.37 (s, 1H), 8.16 (d, 1H), 7.69 (d, 1H), 6.40 (bs, 2H) |
| 107. | 7.71 (bs, 2H), 7.62 (dd, 1H), 7.49 (d, 1H), 7.41 (dd, 1H) |
| 110. | 7.83 (t, 1H), 7.71 (d, 1H), 7.70 (bs, 2H), 7.51 (d, 1H) |
| 137. | 7.60 (bs, 2H), 7.51 (s, 2H), 3.93 (s, 3H), |
| 168. | 7.65-7.30 (m, 6H) |
| 174. | 7.85 (bs, 2H), 7.61 (m, 3H) |
| 186. | 7.80 (s, 1H), 7.66 (d, 1H), 7.59 (d, 1H), 7.58 (bs, 2H) |
| 200. | 7.50-6.92 (m, 5H), 2.41 (s, 3H), 2.32 (s, 3H) |
| 201. | 8.00-7.60 (m, 3H), 7.53 (s, 1H), 7.33 (s, 1H) |
| 204. | 8.10 (bs, 2H), 7.94 (d, 1H), 7.83 (d, 1H), 7.39 (t, 1H), 2.28 (s, 3H) |
| 205. | 7.90 (m, 2H), 7.37 (m, 1H), 7.21 (bs, 2H), 2.30 (s, 3H) |
| 206. | 9.01 (s, 1H), 8.62 (d, 1H), 8.27 (d, 1H), 7.72 (t, 1H), 6.49 (bs, 2H) |
| 207. | 7.85 (d, 1H), 7.71 (bs, 2H), 7.41 (d, 1H), 7.52 (t, 1H) |
| 208. | 7.82 (d, 1H), 7.80-7.55 (m, 4H) |
| 209. | 7.70 (t, 1H), 7.08 (m, 2H), 2.34 (s, 3H) |
| 236. | 4.94 (bs, 2H) |
| 248. | 7.62 (bs, 2H), 2.23 (bs, 1H), 1.00 (m, 4H) |
| 249. | 12.40 (bs, 1H), 7.50 (bs, 2H), 2.12 (m, 1H), 1.01 (m, 4H) |
| 253. | 8.39 (bs, 2H), 1.98 (m, 1H), 1.09 (m, 4H) |
| 265. | 7.32 (bs, 2H), 2.90 (bs, 1H), 1.17 (d, 6H) |
| 272. | 7.66 (bs, 2H), 2.31 (s, 3H) |
| 274. | 7.57 (bs, 2H), 7.30 (m, 5H), 3.96 (bs, 2H) |
| 277. | 7.30 (bs, 2H), 1.28 (s, 9H) |
| 288. | 8.08 (m, 2H), 7.55 (m, 3H), 7.23-6.92 (m, 6H) |
| 296. | 8.04 (d, 2H), 7.28 (d, 2H), 7.22-6.91 (m, 4H), 6.68 (bs, 2H), 2.35 (s, 3H) |
| 304. | 8.21 (d, 2H), 7.48 (d, 2H), 6.36 (bs, 2H) |
| 308. | 8.19 (d, 2H), 7.49 (d, 2H), 7.25-6.91 (m, 4H), 6.50 (bs, 2H) |
| 309. | 8.22 (d, 2H), 7.49 (m, 5H), 6.31 (bs, 2H), 2.38 (s, 3H) |
| 310. | 8.20 (d, 2H), 8.12 (bs, 2H), 7.48 (d, 2H), 6.36 (bs, 2H), 2.53 (s, 6H) |
| 311. | 9.28 (bs, 1H), 8.15 (d, 2H), 7.54 (d, 2H), 6.65 (bs, 2H), 2.78 (s, 9H) |
| 312. | 8.22 (d, 2H), 7.46 (d, 2H), 6.31 (bs, 2H), 3.09 (s, 12H) |
| 318. | 8.38 (d, 2H), 7.81 (d, 2H), 8.21-6.92 (m, 4H), 6.53 (bs, 2H) |
| 332. | 8.02 (m, 1H), 7.89 (m, 1H), 7.48 (m, 1H), 7.27 (m, 1H), 7.22-6.93 (m, 4H), 6.53 (bs, 2H) |
| 333. | 8.09 (m, 2H), 7.55 (m, 2H), 7.23-6.93 (m, 4H), 6.86 (bs, 2H) |
| 335. | 8.61 (s, 1H), 8.42 (d, 1H), 7.82 (d, 1H), 7.22-6.92 (m, 4H), 6.59 (bs, 2H) |
| 340. | 8.41 (s, 1H), 8.21 (d, 1H), 7.52 (d, 1H) |
| 345. | 7.81 (m, 1H), 7.54 (d, 1H), 7.40 (d, 1H), 7.20-6.80 (m, 6H) |
| 359. | 7.49 (m, 2H), 7.32 (bs, 2H), 7.19-6.91 (m, 4H), 3.91 (s, 3H) |
| 369. | 7.60-7.40 (m, 4H), 7.20-6.92 (m, 4H) |
| 371. | 7.49 (m, 2H), 7.42 (m, 1H), 7.22-6.92 (m, 4H), 6.57 (bs, 2H) |
| 375. | 7.62 (s, 1H), 7.55 (d, 1H), 7.46 (d, 1H), 7.21-6.90 (m, 4H), 6.55 (bs, 2H) |
| 381. | 8.25 (d, 2H), 7.90 (d, 2H), 7.24-6.92 (m, 4H), 6.40 (bs, 2H) |
| 383. | 7.88 (m, 1H), 7.60-7.36 (m, 3H), 7.28 (m, 1H), 7.21-6.92 (m, 4H) |
| 387. | 7.51 (m, 1H), 7.21-6.91 (m, 4H), 6.42 (bs, 2H), 2.30 (s, 3H) |
| 392. | 7.75 (m, 1H), 7.62 (d, 1H), 7.52 (d, 1H), 7.24-6.92 (m, 4H), 6.70 (bs, 2H) |
| 454. | 7.32-7.17 (m, 5H), 6.16 (bs, 2H), 3.64 (s, 2H) |
| 461. | 5.92 (bs, 2H), 1.17 (s, 9H) |
| 463. | 7.26-6.86 (m, 4H), 6.70 (bs, 2H) |

Method: $^1$H-NMR (Bruker DRX-400, 400 MHz, 294 K, DMSO-$d_6$, TMS=0.0 ppm)

TABLE 5

Compounds of the formula (II)

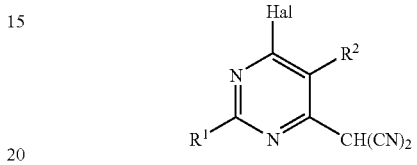

(II)

| Ex. No. | R$^1$ | R$^2$ | Hal |
|---|---|---|---|
| 464. | Ph | Cl | F |
| 465. | Ph | Br | F |
| 466. | Ph | Cl | Cl |
| 467. | Ph | Br | Cl |
| 468. | Ph | Cl | Br |
| 469. | Ph | Br | Br |
| 470. | 4-OMe—Ph | Cl | Cl |
| 471. | 4-OMe—Ph | Br | Cl |
| 472. | 4-NO$_2$—Ph | Cl | Cl |
| 473. | 4-NO$_2$—Ph | Br | Cl |
| 474. | 4-Me—Ph | Cl | Cl |
| 475. | 4-Me—Ph | Br | Cl |
| 476. | 4-I—Ph | Cl | Cl |
| 477. | 4-I—Ph | Br | Cl |
| 478. | 4-F—Ph | Cl | Cl |
| 479. | 4-F—Ph | Br | Cl |
| 480. | 4-Cl—Ph | Cl | Cl |
| 481. | 4-Cl—Ph | Br | Cl |
| 482. | 4-CF$_3$—Ph | Cl | Cl |
| 483. | 4-CF$_3$—Ph | Br | Cl |
| 484. | 4-Br—Ph | Cl | Cl |
| 485. | 4-Br—Ph | Br | Cl |
| 486. | 3-OMe-4-F—Ph | Cl | Cl |
| 487. | 3-OMe-4-F—Ph | Br | Cl |
| 488. | 3-Me—Ph | Cl | Cl |
| 489. | 3-Me—Ph | Br | Cl |
| 490. | 3-Me-4-Cl—Ph | Cl | Cl |
| 491. | 3-Me-4-Cl—Ph | Br | Cl |
| 492. | 3-F—Ph | Cl | Cl |
| 493. | 3-F—Ph | Br | Cl |
| 494. | 3-Cl—Ph | Cl | Cl |
| 495. | 3-Cl—Ph | Br | Cl |
| 496. | 3-CF$_3$—Ph | Cl | Cl |
| 497. | 3-CF$_3$—Ph | Br | Cl |
| 498. | 3-CF$_3$-4-Cl—Ph | Cl | Cl |
| 499. | 3-CF$_3$-4-Cl—Ph | Br | Cl |
| 500. | 3,6-di-Cl—Ph | Cl | Cl |
| 501. | 3,6-di-Cl—Ph | Br | Cl |
| 502. | 3,5-di-Cl—Ph | Cl | Cl |
| 503. | 3,5-di-Cl—Ph | Br | Cl |
| 504. | 3,5-di-CF$_3$—Ph | Cl | Cl |
| 505. | 3,5-di-CF$_3$—Ph | Br | Cl |
| 506. | 3,4-di-OMe—Ph | Cl | Cl |
| 507. | 3,4-di-OMe—Ph | Br | Cl |
| 508. | 3,4-di-Cl—Ph | Cl | Cl |
| 509. | 3,4-di-Cl—Ph | Br | Cl |
| 510. | 2-F-6-Cl—Ph | Cl | Cl |
| 511. | 2-F-6-Cl—Ph | Br | Cl |
| 512. | 2-F-4-Cl—Ph | Cl | Cl |
| 513. | 2-F-4-Cl—Ph | Br | Cl |
| 514. | 2-F-4-Cl-5-OMe—Ph | Cl | Cl |
| 515. | 2-F-4-Cl-5-OMe—Ph | Br | Cl |
| 516. | 2-F-4,5-di-Cl—Ph | Cl | Cl |
| 517. | 2-F-4,5-di-Cl—Ph | Br | Cl |
| 518. | 2-F-3-SMe-4-Cl—Ph | Cl | Cl |

TABLE 5-continued

Compounds of the formula (II)

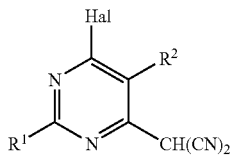

| Ex. No. | R¹ | R² | Hal |
|---|---|---|---|
| 519. | 2-F-3-SMe-4-Cl—Ph | Br | Cl |
| 520. | 2-F-3-OMe-4-Cl—Ph | Cl | Cl |
| 521. | 2-F-3-OMe-4-Cl—Ph | Br | Cl |
| 522. | 2-F-3-OEt-4-Cl—Ph | Cl | Cl |
| 523. | 2-F-3-OEt-4-Cl—Ph | Br | Cl |
| 524. | 2-F-3-OCF₃-4-Cl—Ph | Cl | Cl |
| 525. | 2-F-3-OCF₃-4-Cl—Ph | Br | Cl |
| 526. | 2-F-3-NMe₂-4-Cl—Ph | Cl | Cl |
| 527. | 2-F-3-NMe₂-4-Cl—Ph | Br | Cl |
| 528. | 2-F-3-Me-4-Cl—Ph | Cl | Cl |
| 529. | 2-F-3-Me-4-Cl—Ph | Br | Cl |
| 530. | 2-Cl—Ph | Cl | Cl |
| 531. | 2-Cl—Ph | Br | Cl |
| 532. | 2,6-di-F-3-OMe-4-Cl—Ph | Cl | Cl |
| 533. | 2,6-di-F-3-OMe-4-Cl—Ph | Br | Cl |
| 534. | 2,6-di-Cl—Ph | Cl | Cl |
| 535. | 2,6-di-Cl—Ph | Br | Cl |
| 536. | 2,5-di-Cl—Ph | Cl | Cl |
| 537. | 2,5-di-Cl—Ph | Br | Cl |
| 538. | 2,4-di-F-5-OMe—Ph | Cl | Cl |
| 539. | 2,4-di-F-5-OMe—Ph | Br | Cl |
| 540. | 2,4-di-F-3-OMe—Ph | Cl | Cl |
| 541. | 2,4-di-F-3-OMe—Ph | Br | Cl |
| 542. | 2,4-di-Cl—Ph | Cl | Cl |
| 543. | 2,4-di-Cl—Ph | Br | Cl |
| 544. | 2,4-di-Cl-5-F—Ph | Cl | Cl |
| 545. | 2,4-di-Cl-5-F—Ph | Br | Cl |
| 546. | 2,4-di-Cl-3-OMe—Ph | Cl | Cl |
| 547. | 2,4-di-Cl-3-OMe—Ph | Br | Cl |
| 548. | 2,4,6-tri-Cl—Ph | Cl | Cl |
| 549. | 2,4,6-tri-Cl—Ph | Br | Cl |
| 550. | 1-Cl—cPr | Cl | Cl |
| 551. | 1-Cl—cPr | Br | Cl |
| 552. | 2-cPr—Vin | Cl | Cl |
| 553. | 2-cPr—Vin | Br | Cl |
| 554. | 2-di-Me—cPr | Cl | Cl |
| 555. | 2-di-Me—cPr | Br | Cl |
| 556. | 2-Me—Vin | Cl | Cl |
| 557. | 2-Me—Vin | Br | Cl |
| 558. | 2-Ph—Vin | Cl | Cl |
| 559. | 2-Ph—Vin | Br | Cl |
| 560. | 4-Cl—PhCH₂ | Cl | Cl |
| 561. | 4-Cl—PhCH₂ | Br | Cl |
| 562. | cBu | Cl | Cl |
| 563. | cBu | Br | Cl |
| 564. | CF₃ | Cl | Cl |
| 565. | CF₃ | Br | Cl |
| 566. | cHex | Cl | Cl |
| 567. | cHex | Br | Cl |
| 568. | cPr | Cl | Cl |
| 569. | cPr | Br | Cl |
| 570. | Hex | Cl | Cl |
| 571. | Hex | Br | Cl |
| 572. | iPr | Cl | Cl |
| 573. | iPr | Br | Cl |
| 574. | Me | Cl | F |
| 575. | Me | Br | F |
| 576. | Me | Cl | Cl |
| 577. | Me | Br | Cl |
| 578. | Me | Cl | Br |
| 579. | Me | Br | Br |
| 580. | PhCH₂ | Cl | Cl |
| 581. | PhCH₂ | Br | Cl |
| 582. | tBu | Cl | Cl |
| 583. | tBu | Br | Cl |
| 584. | Vin | Cl | Cl |
| 585. | Vin | Br | Cl |

TABLE 5-continued

Compounds of the formula (II)

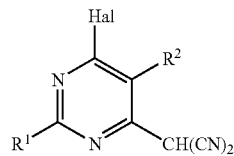

| Ex. No. | R¹ | R² | Hal |
|---|---|---|---|
| 586. | 2,4-di-Me—Ph | Cl | Cl |
| 587. | 2,4-di-F—Ph | Cl | Cl |
| 588. | 4-COOEt—Ph | Cl | Cl |
| 589. | 2-F-4-Me—Ph | Cl | Cl |
| 590. | 3-F-4-Me—Ph | Cl | Cl |
| 591. | 3-Me-4-F—Ph | Cl | Cl |

Physical data of selected compounds from Table 5:

| Ex. No. | Data |
|---|---|
| 472. | 8.43 (d, 2H), 8.35 (d, 2H) |
| 478. | 8.25 (m, 2H), 7.30 (m, 2H) |
| 480. | 8.21 (d, 2H), 7.54 (d, 2H) |
| 492. | 8.19-8.14 (m, 2H), 7.59-7.48 (m, 2H) |
| 494. | 8.16 (m, 2H), 7.53 (m, 2H) |
| 510. | 7.51 (m, 1H), 7.41 (m, 1H), 7.33 (m, 1H) |
| 534. | 7.58-7.53 (d, 2H), 7.50-7.45 (m, 1H) |
| 542. | 7.68 (m, 2H), 7.50 (d, 1H) |
| 576. | 2.28 (s, 3H) |
| 586. | 7.67 (d, 1H), 7.07 (m, 2H), 2.50 (s, 3H), 2.30 (s, 3H) |
| 587. | 7.98 (m, 1H), 7.29 (m, 1H), 7.19 (m, 1H) |
| 588. | 8.33 (d, 2H), 8.05 (d, 2H), 4.35 (q, 2H), 1.33 (t, 3H) |
| 589. | 7.80 (m, 1H), 7.09 (m, 2H), 2.35 (s, 3H) |
| 590. | 7.94 (dd, 1H), 7.83 (dd, 1H), 7.38 (m, 1H), 2.29 (s, 3H) |
| 591. | 8.08 (m, 2H), 7.22 (m, 1H), 2.28 (s, 3H) |

Method: ¹H-NMR (Bruker DRX-400, 400 MHz, 294 K, DMSO-d₆, TMS=0.0 ppm)

B. Formulation Examples a) A dusting composition is obtained by mixing 10 parts by weight of a compound according to the invention and 90 parts by weight of talc as inert substance and comminuting in an impact mill.

b) A readily water-dispersible, wettable powder is obtained by mixing 25 parts by weight of a compound according to the invention, 64 parts by weight of kaolin-containing quartz as inert substance, 10 parts by weight of potassium lignosulfonate and 1 part by weight of sodium oleoylmethyltaurate as wetting agent and dispersant and grinding in a pin mill.

c) A readily water-dispersible dispersion concentrate is obtained by mixing 20 parts by weight of a compound according to the invention with 6 parts by weight of alkylphenol polyglycol ether (®Triton X 207), 3 parts by weight of isotridecanol polyglycol ether (8 EO) and 71 parts by weight of paraffinic mineral oil (boiling range e.g. ca. 255 to above 277° C.) and grinding in an attrition ball mill to a fineness of below 5 microns.

d) An emulsifiable concentrate is obtained from 15 parts by weight of a compound according to the invention, 75 parts by weight of cyclohexanone as solvent and 10 parts by weight of oxethylated nonylphenol as emulsifier.

e) Water-dispersible granules are obtained by mixing
   75 parts by weight of a compound according to the invention,
   10 parts by weight of calcium lignosulfonate,
   5 parts by weight of sodium lauryl sulfate,
   3 parts by weight of polyvinyl alcohol and
   7 parts by weight of kaolin,
   grinding on a pin mill and granulating the powder in a fluidized bed by spraying on water as granulation liquid.
f) Water-dispersible granules are also obtained by homogenizing and precomminuting
   25 parts by weight of a compound according to the invention
   5 parts by weight of sodium 2,2'-dinaphthylmethane-6,6'-disulfonate
   2 parts by weight of sodium oleoylmethyltaurate,
   1 part by weight of polyvinyl alcohol,
   17 parts by weight of calcium carbonate and
   50 parts by weight of water
   on a colloid mill, then grinding on a bead mill and atomizing and drying the suspension obtained in this way in a spray tower by means of a single-material nozzle.

C. Biological Examples

Herbicidal Effect and Crop Plant Compatibility Post-Emergence

Seeds of mono- and dicotyledonous weed plants and crop plants are planted in wood-fiber pots in sandy loam, covered with earth and grown in a greenhouse under good growth conditions. 2 to 3 weeks after sowing, the test plants are treated in the single-leaf stage. The compounds according to the invention, formulated in the form of wettable powders (WP) or as emulsion concentrates (EC), are then sprayed onto the green plant parts as aqueous suspension or emulsion using an application rate of 600 to 800 l of water/ha (converted) with the addition of 0.2% by weight of wetting agent. After the test plants had been in the greenhouse for ca. 3 weeks under optimum growth conditions, the effect of the preparations is scored visually in comparison with untreated controls (herbicidal effect in percent (%): 100% effect=plants have died off, 0% effect=as control plants).

As the results in Table 7 show, compounds according to the invention have good herbicidal post-emergence effectiveness in respect of a broad spectrum of weed grasses and broad-leaved weeds. For example, compound No. 1 and other compounds from Tables 1 to 4 have a very good herbicidal effect of at least 80% in respect of harmful plants such as *Matricaria inodora, Polygonum (Fallopia) convolvulus* and *Veronica persica* post-emergence at an application rate of 0.32 kg and less of active substance per hectare. At the same time, compounds according to the invention leave graminaceous crops such as barley, wheat, rye, millet, corn or rice undamaged in the post-emergence method even at high dosages of active ingredient. Moreover, some substances also protect dicotyledonous crops such as soybean, cotton, rapeseed, sugarbeet or potatoes. Some of the compounds according to the invention exhibit high selectivity and are therefore suitable post-emergence for controlling undesired plant growth in agricultural crops.

Herbicidal Effect and Crop Plant Compatibility Pre-Emergence

Seeds of mono- and dicotyledonous weed plants and crop plants are planted in wood-fiber pots in sandy loam and covered with earth. The compounds according to the invention, formulated in the form of wettable powders (WP) or as emulsion concentrates (EC), are then applied to the surface of the covering earth as aqueous suspension or emulsion at an application rate corresponding to 320 g/hectare at an application rate of 600 to 800 l of water/ha (converted) with the addition of 0.2% wetting agent.

Following treatment, the pots are placed in a greenhouse and kept under good growth conditions for the test plants. The visual grading of the damage to the test plants is carried out after a test time of 3 weeks in comparison to untreated controls (herbicidal effect in percent (%): 100% effect=plants have died off, 0% effect=as control plants).

As the results in Table 6 show, compounds according to the invention have good herbicidal pre-emergence effectiveness in respect of a broad spectrum of weed grasses and broad-leaved weeds. For example, compounds No. 9 and other compounds from Tables 1 to 4 have a very good herbicidal effect in respect of harmful plants such as *Sinapis alba, Avena fatua, Stellaria media, Echinochloa crus-galli, Lolium multiflorum, Setaria viridis, Abutilon theophrasti, Amaranthus retroflexus* and *Alopecurus myosuroides* in the pre-emergence method at an application rate of 0.32 kg of active substance per hectare. At the same time, compounds according to the invention leave dicotyledonous crops such as soybean, cotton, rapeseed, sugarbeet and potatoes undamaged in the pre-emergence method even at high dosages of active ingredient. Moreover, some substances also protect graminaceous cultures such as barley, wheat, rye, millet, corn or rice. Some of the compounds according to the invention exhibit high selectivity and are therefore suitable pre-emergence for controlling undesired plant growth in agricultural crops.

TABLE 6

Biological effect pre-emergence

Effect in % in respect of stated plant

| Compound | ABUTH | ALOMY | AMARE | LOLMU | MATIN | PHBPU | POLCO | SETVI | VERPE | VIOTR |
|---|---|---|---|---|---|---|---|---|---|---|
| 9 | | | | | | | | | 80 | 90 |
| 12 | 80 | | 100 | | | | | | 100 | |
| 29 | | | | | | | | | 100 | 80 |
| 41 | | | | | 80 | | | | | 100 |
| 110 | | | 100 | | | | | 80 | 100 | 90 |
| 186 | | | 90 | | | | | | 100 | |
| 202 | | | 90 | | 100 | | | | 100 | |
| 203 | | | 100 | | | | | | 90 | |
| 205 | | | | | | | | | 100 | 100 |
| 208 | 100 | | 80 | | | | | 90 | 100 | |
| 210 | | | | | | | | | 80 | 100 |
| 248 | | | | | 80 | 80 | | | 90 | |

TABLE 6-continued

Biological effect pre-emergence

Effect in % in respect of stated plant

| Compound | ABUTH | ALOMY | AMARE | LOLMU | MATIN | PHBPU | POLCO | SETVI | VERPE | VIOTR |
|---|---|---|---|---|---|---|---|---|---|---|
| 249 | 90 | | 90 | | 90 | 85 | 90 | | 90 | 95 |
| 296 | 80 | | 100 | | | | | | 100 | |
| 304 | | | 90 | | 80 | | | 80 | 100 | |
| 308 | 80 | 80 | 100 | | 90 | 95 | 90 | 90 | 100 | 100 |
| 309 | | | 85 | | | | | | 100 | 100 |
| 310 | | | 100 | | 80 | | | 90 | 100 | 100 |
| 311 | 80 | | 100 | | 90 | | | 90 | 100 | 100 |
| 312 | | | 95 | | | | | 90 | 100 | 100 |
| 318 | | | | | | | 80 | | 100 | |
| 321 | | | 90 | | | | | | 100 | 100 |
| 335 | | | | | 80 | | | | 100 | 80 |
| 345 | 90 | 80 | 90 | | 80 | | | 80 | 100 | 80 |
| 359 | 90 | | 100 | 80 | 100 | | | 90 | 100 | |
| 375 | | | 100 | | | | | | 100 | 80 |
| 387 | | 80 | | | | | | | 100 | |
| 392 | | | 80 | | | | | | 100 | 100 |
| 455 | | | | 80 | | | | | | 100 |

Abbreviations:
ABUTH *Abutilon theophrasti*
ALOMY *Alopecurus myosuroides*
AMARE *Amaranthus retroflexus*
LOLMU *Lolium multiflorum*
MATIN *Tripleurospermum inodorum*
PHBPU *Ipomoea purpurea*
POLCO *Polygonum convolvulus*
SETVI *Setaria viridis*
VERPE *Veronica persica*
VIOTR *Viola tricolor*

ABBREVIATIONS

ABUTH *Abutilon* theophrasti
ALOMY *Alopecurus* myosuroides
AMARE *Amaranthus retroflexus*
LOLMU *Lolium muitiflorum*
MATIN *Tripleurospermum inodorum*
PHBPU *Ipomoea purpurea*
POLCO *Polygonum convolvulus*
SETVI *Setaria viridis*
VERPE *Veronica persica*
VIOTR *Viola tricolor*

TABLE 7

Biological effect post-emergence

Effect in % in respect of stated plant

| Compound | ABUTH | AMARE | ECHCG | MATIN | PHBPU | POLCO | SETVI | STEME | VERPE | VIOTR |
|---|---|---|---|---|---|---|---|---|---|---|
| 12 | 80 | 90 | 80 | 80 | | 80 | | | 90 | |
| 29 | 80 | | | | | | | | 90 | 80 |
| 45 | | | | | | 80 | | 80 | 90 | 80 |
| 87 | | | | 90 | | | | | 90 | |
| 104 | 80 | 90 | 80 | 90 | | 80 | 80 | | 90 | 80 |
| 110 | | 90 | 80 | 90 | 80 | 95 | 80 | 90 | 90 | 90 |
| 186 | 100 | 100 | | 90 | | 100 | | 90 | 90 | 80 |
| 201 | | 90 | | 80 | | 90 | | | 90 | |
| 202 | 90 | 100 | 90 | 80 | | 90 | | | | |
| 204 | 90 | 90 | 80 | 80 | | 80 | | | 80 | |
| 207 | 80 | 100 | | 80 | | 100 | | 80 | 90 | |
| 208 | 90 | 100 | | 100 | 80 | 80 | | 90 | 90 | 90 |
| 210 | | 90 | | | | | | | 80 | |
| 240 | 80 | | | 80 | | | | | 90 | |
| 248 | | 80 | | 80 | | | | 80 | 90 | |
| 249 | 83 | 93 | 90 | 90 | 90 | 90 | | 80 | 100 | 87 |
| 265 | 80 | 100 | | 90 | 100 | 90 | | 90 | 90 | |
| 296 | 80 | 90 | 80 | 90 | | | | | 90 | |
| 300 | | 80 | | 80 | | | | | 80 | |
| 304 | 80 | 100 | | 90 | | 80 | | 80 | | 80 |
| 308 | 93 | 100 | 88 | 93 | 90 | 100 | 87 | 92 | 97 | 88 |
| 309 | 90 | 95 | 90 | 85 | | 90 | 80 | 80 | 90 | 85 |
| 310 | 85 | 95 | 90 | 85 | 80 | 85 | 80 | 80 | 87 | 90 |
| 311 | 90 | 90 | 90 | 90 | | 90 | 80 | 80 | 90 | 80 |
| 312 | 85 | 90 | 85 | 90 | | 90 | 90 | 80 | 95 | 80 |
| 313 | 80 | 100 | | 90 | | | | 90 | 100 | 80 |

TABLE 7-continued

Biological effect post-emergence

| Compound | Effect in % in respect of stated plant | | | | | | | | | |
|---|---|---|---|---|---|---|---|---|---|---|
| | ABUTH | AMARE | ECHCG | MATIN | PHBPU | POLCO | SETVI | STEME | VERPE | VIOTR |
| 318 | 80 | | | 90 | | 80 | | | 90 | |
| 321 | 90 | 100 | 90 | 100 | | 100 | 80 | 80 | 90 | 90 |
| 335 | | 80 | | 80 | | | | | | |
| 340 | 80 | 90 | | 90 | | 90 | | | 90 | |
| 345 | | 100 | | 90 | 90 | 80 | | 90 | 90 | 80 |
| 359 | 80 | 100 | 90 | 90 | 80 | 90 | 80 | | | |
| 375 | 90 | 100 | | 90 | | 100 | | | 90 | |
| 383 | 80 | 90 | | 90 | | 100 | | | 90 | |
| 385 | 80 | 100 | | 80 | | 80 | | | | |
| 387 | 90 | 100 | 90 | | | 100 | | | 80 | |
| 389 | 80 | 80 | | | | 80 | | | 80 | |
| 390 | | 90 | | | | 80 | | | 80 | |
| 391 | | | | | | 80 | | | | |
| 392 | 90 | 100 | 80 | 100 | | 90 | 80 | 90 | 90 | 90 |

Abbreviations: See Table 6, moreover:
ECHCG *Echinochloa crus-galli*
STEME *Stellaria media*

Abbreviations: see Table 6, moreover:
ECHCG *Echinochloa crus-galli*
STEME *Stellaria media*

The invention claimed is:

1. A compound of formula (I) or an N-oxide or an agrochemically suitable salt thereof,

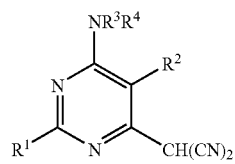

(I)

in which the radicals have the following meaning:

$R^1$ is phenyl, optionally substituted with 1-3 radicals $R^x$, which, independently of one another, are halogen, carboxyl, cyano, nitro, $(C_1-C_6)$alkyl, $(C_1-C_6)$haloalkyl, $(C_1-C_4)$hydroxyalkyl, $(C_2-C_4)$alkoxyalkyl, $(C_2-C_4)$haloalkoxyalkyl, $(C_2-C_4)$alkenyl, $(C_2-C_4)$haloalkenyl, $(C_2-C_4)$alkynyl, $(C_3-C_4)$haloalkynyl, hydroxy, $(C_1-C_4)$alkoxy, $(C_1-C_4)$haloalkoxy, $(C_2-C_4)$alkenyloxy, $(C_2-C_4)$haloalkenyloxy, $(C_2-C_4)$alkynyloxy, $(C_3-C_4)$haloalkynyloxy, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_2-C_4)$alkenylthio, $(C_2-C_4)$haloalkenylthio, $(C_2-C_4)$alkenylsulfinyl, $(C_2-C_4)$haloalkenylsulfinyl, $(C_2-C_4)$alkenylsulfonyl, $(C_2-C_4)$haloalkenylsulfonyl, $(C_2-C_4)$alkynylthio, $(C_3-C_4)$haloalkynylthio, $(C_3-C_4)$alkynylsulfinyl, $(C_3-C_4)$haloalkynylsulfinyl, $(C_3-C_4)$alkynylsulfonyl, $(C_3-C_4)$haloalkynylsulfonyl, $(C_1-C_6)$alkylamino, $(C_2-C_8)$dialkylamino, $(C_2-C_6)$alkylcarbonyl, $(C_2-C_6)$alkoxycarbonyl, $(C_2-C_6)$alkylaminocarbonyl, $(C_3-C_8)$dialkylaminocarbonyl, $(C_3-C_6)$trialkylsilyl, phenyl, phenoxy or a 5- or 6-membered heteroaromatic ring, each phenyl ring, phenoxy ring or 5- or 6-membered heteroaromatic ring optionally substituted with 1-3 substituents independently of one another selected from $R^{28}$; or two adjacent radicals $R^x$ together form a group —OCH$_2$O—, —CH$_2$CH$_2$O—, —OCH$_2$CH$_2$O—, —OCH(CH$_3$)O—, —OC(CH$_3$)$_2$O—, —OCF$_2$O—, —CF$_2$CF$_2$O—, —OCF$_2$CF$_2$O— or —CH=CH—CH=CH—; or $(C_1-C_6)$-alkyl, optionally substituted with 1-3 radicals $R^y$, which, independently of one another, are halogen, $(C_2-C_6)$alkenyl, $(C_2-C_6)$haloalkenyl, $(C_1-C_3)$alkoxy, $(C_1-C_2)$haloalkoxy, $(C_1-C_3)$alkylthio, $(C_1-C_2)$haloalkylthio or optionally substituted aryl; or $(C_2-C_6)$-alkenyl, optionally substituted with 1-3 radicals $R^z$, which, independently of one another, are halogen, $(C_1-C_6)$alkyl, $(C_1-C_6)$haloalkyl, $(C_1-C_3)$alkoxy, $(C_1-C_2)$haloalkoxy, $(C_1-C_3)$alkylthio or $(C_1-C_2)$haloalkylthio;

$R^2$ is H, F, Cl, Br, I, CN, NO$_2$, OR$^5$, SR$^6$ or N(R$^7$)R$^8$; in which R$^5$ is H, $(C_1-C_4)$alkyl or $(C_1-C_3)$haloalkyl, R$^6$ is H, $(C_1-C_4)$alkyl or $(C_1-C_3)$haloalkyl and R$^7$ and R$^8$, independently of one another, are H or $(C_1-C_4)$alkyl;

$R^3$ is H, $(C_1-C_4)$alkyl optionally substituted with 1-2 radicals R$^9$, $(C_2-C_4)$alkenyl optionally substituted with 1-2 radicals R$^{10}$, or $(C_2-C_4)$alkynyl optionally substituted with 1-2 radicals R$^{11}$; or R$^3$ is C(=O)R$^{12}$, NO$_2$, OR$^{13}$, S(O)$_2$R$^{14}$, N(R$^{15}$)R$^{16}$ or N=C(R$^{17}$)R$^{18}$;

$R^4$ is H, $(C_1-C_4)$alkyl optionally substituted with 1-2 radicals R$^9$, or C(=O)R$^{12}$; or $R^3$ and $R^4$ together form a group —(CH$_2$)$_4$—, —(CH$_2$)$_5$—, —CH$_2$CH=CHCH$_2$— or —(CH$_2$)$_2$O(CH$_2$)$_2$—, each group optionally substituted with 1-2 radicals R$^{19}$; or $R^3$ and $R^4$ together form a group =(R$^{20}$)N(R$^{21}$)R$^{22}$ or =C(R$^{23}$)OR$^{24}$;

here, each radical R$^9$, R$^{10}$ and R$^{11}$, independently of the others, is halogen, $(C_1-C_3)$alkoxy, $(C_1-C_3)$haloalkoxy, $(C_1-C_3)$alkylthio, $(C_1-C_3)$haloalkylthio, amino, $(C_1-C_3)$alkylamino, $(C_2-C_4)$dialkylamino or $(C_2-C_4)$alkoxycarbonyl;

$R^{12}$ is in each case independently of the others H, $(C_1-C_4)$alkyl, $(C_1-C_3)$haloalkyl, $(C_1-C_4)$alkoxy, phenyl, phenoxy or benzyloxy;

$R^{13}$ is H, $(C_1-C_4)$alkyl, $(C_1-C_3)$haloalkyl or CHR$^{25}$C(O)OR$^{26}$;

$R^{14}$ is $(C_1-C_4)$alkyl or $(C_1-C_3)$haloalkyl;

$R^{15}$ is H, $(C_1-C_4)$alkyl or C(=O)R$^{27}$;

$R^{16}$ is H or $(C_1-C_4)$alkyl;

$R^{17}$ is H, $(C_1-C_4)$alkyl or phenyl optionally substituted with 1-3 radicals, which, independently of one another, are CH$_3$, Cl or OCH$_3$;

$R^{18}$ is H or $(C_1-C_4)$alkyl; or $R^{17}$ and $R^{18}$ together form a group —$(CH_2)_4$— or —$(CH_2)_5$—;

$R^{19}$ is, in each case independently of the others, halogen, $(C_1-C_3)$alkyl, $(C_1-C_3)$alkoxy, $(C_1-C_3)$haloalkoxy, $(C_1-C_3)$alkylthio, $(C_1-C_3)$haloalkylthio, amino, $(C_1-C_3)$alkylamino, $(C_2-C_4)$dialkylamino or $(C_2-C_4)$alkoxycarbonyl;

$R^{20}$ is H or $(C_1-C_4)$alkyl;

$R^{21}$ and $R^{22}$, independently of one another, are H or $(C_1-C_4)$alkyl; or $R^{21}$ and $R^{22}$ together form a group —$(CH_2)_4$—, —$(CH_2)_5$—, —$CH_2CH=CHCH_2$— or —$(CH_2)_2O(CH_2)_2$—;

$R^{23}$ is H or $(C_1-C_4)$alkyl;

$R^{24}$ is $(C_1-C_4)$alkyl;

$R^{25}$ is H, $(C_1-C_4)$alkyl, $(C_1-C_3)$haloalkyl, $(C_1-C_4)$alkoxy, phenyl, phenoxy or benzyloxy;

$R^{26}$ is H, $(C_1-C_4)$alkyl or $(C_1-C_4)$alkoxy;

$R^{27}$ is H, $(C_1-C_4)$alkyl or benzyl; and $R^{28}$ is, in each case independently of the others, halogen, cyano, nitro, $(C_1-C_6)$alkyl, $(C_1-C_6)$haloalkyl, $(C_2-C_4)$alkenyl, $(C_2-C_4)$haloalkenyl, $(C_3-C_4)$alkynyl, $(C_3-C_4)$haloalkynyl, $(C_1-C_4)$alkoxy, $(C_1-C_4)$haloalkoxy, $(C_1-C_4)$alkylthio, $(C_1-C_4)$haloalkylthio, $(C_1-C_4)$alkylsulfinyl, $(C_1-C_4)$alkylsulfonyl, $(C_1-C_4)$alkylamino, $(C_2-C_8)$dialkylamino, $(C_2-C_4)$alkylcarbonyl, $(C_2-C_6)$alkoxycarbonyl, $(C_2-C_6)$alkylaminocarbonyl, $(C_3-C_8)$dialkylaminocarbonyl or $(C_3-C_6)$trialkylsilyl.

2. A compound of the formula (I), or N-oxide or agrochemically suitable salt thereof as claimed in claim 1, in which the radicals have the following meaning.

$R^1$ is phenyl, optionally substituted with 1-3 radicals $R^x$, which, independently of one another, are halogen, carboxyl, cyano, nitro, $(C_1-C_6)$alkyl, $(C_1-C_6)$haloalkyl, $(C_2-C_4)$alkoxyalkyl, $(C_2-C_4)$haloalkoxyalkyl, $(C_2-C_4)$alkenyl, $(C_2-C_4)$haloalkenyl, $(C_2-C_4)$alkynyl, $(C_3-C_4)$haloalkynyl, hydroxy, $(C_1-C_4)$alkoxy, $(C_1-C_4)$haloalkoxy, $(C_1-C_4)$alkylthio, $(C_1-C_4)$haloalkylthio, $(C_1-C_4)$alkylsulfinyl, $(C_1-C_4)$alkylsulfonyl, $(C_1-C_6)$alkylamino, $(C_2-C_8)$dialkylamino, —$OCH_2O$—, —$CH_2CH_2O$—, —$OCH_2CH_2O$—, —$OCH(CH_3)O$—, —$OC(CH_3)_2O$—, —$OCF_2O$—, —$CF_2CF_2O$— or —$OCF_2CF_2O$—, where the eight last-mentioned substituents are formed in each case by two adjacent $R^x$; or $(C_1-C_6)$alkyl, optionally substituted with 1-3 radicals $R^y$, which, independently of one another, are halogen, $(C_2-C_6)$alkenyl, $(C_2-C_6)$haloalkenyl, $(C_1-C_3)$alkoxy, $(C_1-C_2)$haloalkoxy, $(C_1-C_3)$alkylthio, $(C_1-C_2)$haloalkylthio or optionally substituted phenyl; or $(C_2-C_6)$alkenyl, optionally substituted with 1-3 radicals $R^z$, which, independently of one another, are halogen, $(C_1-C_6)$alkyl, $(C_1-C_6)$haloalkyl, $(C_1-C_3)$alkoxy, $(C_1-C_2)$haloalkoxy, $(C_1-C_3)$alkylthio or $(C_1-C_2)$haloalkylthio;

$R^2$ is H, F, Cl, Br, I, CN or $NO_2$;

$R^3$ is H, $(C_1-C_4)$alkyl, $(C_2-C_4)$alkenyl, $(C_2-C_4)$alkynyl, $C(=O)R^{12}$, $OR^{13}$, $N(R^{15})R^{16}$ or $N=C(R^{17})R^{18}$;

$R^4$ is H or $(C_1-C_4)$alkyl, optionally substituted with 1-2 radicals $R^9$, or $C(=O)R^{12}$; or $R^3$ and $R^4$ together form a group —$(CH_2)_4$—, —$(CH_2)_5$—, —$(CH_2)_2O(CH_2)_2$— or $=C(R^{20})N(R^{21})R^{22}$;

here, each radical $R^9$, $R^{10}$ and $R^{11}$, independently of the others, is halogen, $(C_1-C_3)$alkoxy, $(C_1-C_3)$haloalkoxy, $(C_1-C_3)$alkylthio, $(C_1-C_3)$haloalkylthio, amino, $(C_1-C_3)$alkylamino, $(C_2-C_4)$dialkylamino or $(C_2-C_4)$alkoxycarbonyl;

$R^{12}$ is, in each case independently of the others, H, $(C_1-C_4)$alkyl, $(C_1-C_3)$haloalkyl, $(C_1-C_4)$alkoxy, phenyl, phenoxy or benzyloxy;

$R^{13}$ is H, $(C_1-C_4)$alkyl, $(C_1-C_3)$haloalkyl or $CHR^{25}C(O)OR^{26}$;

$R^{15}$ is H, $(C_1-C_4)$alkyl or $C(=O)R^{27}$;

$R^{16}$ is H or $(C_1-C_4)$alkyl;

$R^{17}$ is H, $(C_1-C_4)$alkyl or phenyl optionally substituted with 1-3 radicals which, independently of one another, are $CH_3$, Cl or $OCH_3$;

$R^{18}$ is H or $(C_1-C_4)$alkyl; or $R^{17}$ and $R^{18}$ together form a group —$(CH_2)_4$— or —$(CH_2)_5$—;

$R^{20}$ is H or $(C_1-C_4)$alkyl;

$R^{21}$ and $R^{22}$, independently of one another, are H or $(C_1-C_4)$alkyl; or $R^{21}$ and $R^{22}$ together form a group —$(CH_2)_4$—, —$(CH_2)_5$—, —$CH_2CH=CHCH_2$— or —$(CH_2)_2O(CH_2)_2$—;

$R^{25}$ is H, $(C_1-C_4)$alkyl, $(C_1-C_3)$haloalkyl, $(C_1-C_4)$alkoxy, phenyl, phenoxy or benzyloxy; and $R^{26}$ is H, $(C_1-C_4)$alkyl or $(C_1-C_4)$alkoxy.

3. A compound of formula (I) or N-oxide or agrochemically suitable salt thereof as claimed in claim 1, in which the radicals have the following meaning:

$R^1$ is phenyl, optionally substituted with 1-3 radicals $R^x$, which, independently of one another, are halogen, carboxyl, cyano, nitro, $(C_1-C_6)$alkyl, $(C_1-C_6)$haloalkyl, $(C_1-C_4)$alkoxy, $(C_r-C_4)$haloalkoxy, $(C_1-C_6)$alkylamino, $(C_2-C_8)$dialkylamino,
—$OCH_2O$—, —$OCH_2CH_2O$— or —$OCH(CH_3)O$—, where the three last-mentioned substituents are in each case formed by two adjacent $R^x$; or $(C_1-C_6)$alkyl, optionally substituted with 1-3 radicals $R^y$, which, independently of one another, are halogen, $(C_1-C_3)$alkoxy, $(C_1-C_2)$haloalkoxy or unsubstituted phenyl or phenyl substituted by one or more halogens; or $(C_2-C_6)$alkenyl, optionally substituted with 1-3 radicals $R^z$, which, independently of one another, are halogen, $(C_1-C_6)$alkyl, $(C_1-C_6)$haloalkyl, $(C_1-C_3)$alkoxy or $(C_1-C_2)$haloalkoxy;

$R^2$ is F, Cl, Br, I or $NO_2$;

$R^3$ is H, $(C_1-C_4)$alkyl, $(C_2-C_4)$alkenyl, $C(=O)R^{12}$, in which $R^{12}$ is H, $(C_1-C_4)$alkyl, $(C_1-C_3)$haloalkyl, $(C_1-C_4)$alkoxy, phenyl, phenoxy or benzyloxy, or $OR^{13}$, in which $R^{13}$ is H, $(C_1-C_4)$alkyl, $(C_1-C_3)$haloalkyl or $CHR^{25}C(O)OR^{26}$, in which $R^{25}$ is H, $(C_1-C_4)$alkyl, $(C_1-C_3)$haloalkyl, $(C_1-C_4)$alkoxy, phenyl, phenoxy or benzyloxy, and $R^{26}$ is H, $(C_1-C_4)$alkyl or $(C_1-C_4)$alkoxy;

$R^4$ is H or $(C_1-C_4)$alkyl; or $R^3$ and $R^4$ together form a group —$(CH_2)_2O(CH_2)_2$—.

4. A compound of formula (I) or N-oxide or agrochemically suitable salt thereof as claimed in claim 1, in which the radicals have the following meaning:

$R^1$ is phenyl, optionally substituted with 1-3 radicals $R^x$, which, independently of one another, are halogen, cyano, nitro, $(C_1-C_6)$alkyl, $(C_1-C_6)$haloalkyl, $(C_1-C_4)$alkoxy, $(C_1-C_4)$haloalkoxy, $(C_1-C_6)$alkylamino, $(C_2-C_8)$dialkylamino, —$OCH_2O$—, —$OCH_2CH_2O$— or —$OCH(CH_3)O$—; or $(C_1-C_6)$alkyl, optionally substituted with 1-3 radicals $R^y$, which, independently of one another, are halogen, $(C_1-C_3)$alkoxy or $(C_1-C_2)$haloalkoxy; or ($C_2$-$C_6$)alkenyl, optionally substituted with 1-3 radicals $R^z$, which, independently of one another, are halogen, ($C_1$-$C_6$)alkyl, ($C_1$-$C_6$)haloalkyl, ($C_1$-$C_3$)alkoxy or ($C_1$-$C_2$)haloalkoxy;

$R^2$ is F, Cl, Br or I;

$R^3$ is H, ($C_1$-$C_4$)alkyl, ($C_2$-$C_4$)alkenyl, C(=O)$R^{12}$, in which $R^{12}$ is H, ($C_1$-$C_4$)alkyl, ($C_1$-$C_3$)haloalkyl, ($C_1$-$C_4$)alkoxy, phenyl, phenoxy or benzyloxy, or $OR^{13}$, in which $R^{13}$ is H, ($C_1$-$C_4$)alkyl, ($C_1$-$C_3$)haloalkyl or $CHR^{25}C(O)OR^{26}$, in which $R^{25}$ is H, ($C_1$-$C_4$)alkyl, ($C_1$-$C_3$)haloalkyl, ($C_1$-$C_4$)alkoxy, phenyl, phenoxy or benzyloxy, and $R^{26}$ is H, ($C_1$-$C_4$)alkyl or ($C_1$-$C_4$)alkoxy;

$R^4$ is H or ($C_1$-$C_4$)alkyl; or $R^3$ and $R^4$ together form a group —($CH_2$)$_2$O($CH_2$)$_2$—.

5. An agrochemical composition comprising a) at least one compound of formula (I) or N-oxide or agrochemically suitable salt thereof, as defined in claim 1, and b) at least one auxiliary or additive customary in crop protection.

6. An agrochemical composition comprising a) at least one compound of formula (I) or N-oxide or agrochemically suitable salt thereof, as defined in claim 1, b) at least one agrochemical active ingredient different from component a), and optionally c) at least one auxiliary or additive customary in crop protection.

7. A method for controlling an undesired plant or for regulating the growth of a plant, comprising applying an effective amount of at least one compound of formula (I) or an N-oxide or an agrochemically suitable salt thereof, as defined in claim 1, to the plant, or to a seed material or to an area on which the plant grows.

8. A herbicide or plant growth regulator composition comprising at least one compound of the formulation (I) or an N-oxide or an agrochemically suitable salt as claimed in claim 1.

9. A herbicide or plant growth regulator composition as claimed in claim 8, where the compounds of the formula (I) or N-oxide or agrochemically suitable salt thereof is suitable for controlling harmful plants or for growth regulation in plant crops.

10. A herbicide or plant growth regulator as claimed in claim 9, where the crop plants are transgenic or nontransgenic crop plants.

11. A process for the preparation of a compound of formula (I) or N-oxide or agrochemically suitable salt thereof, as defined in claim 1 comprising:

a) reacting a halogen compound of the formula (II)

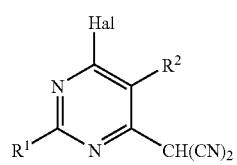

(II)

with an amine of the formula (III) $HNR^3R^4$, where Hal is a halogen atom, and b) optionally converting the compound of the formula (I) in step a) into an N-oxide or an agrochemically suitable salt.

12. A compound of the formula (II)

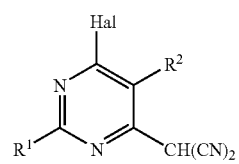

(II)

in which Hal is a halogen atom and $R^1$ is phenyl, optionally substituted with 1-3 radicals $R^x$, which, independently of one another, are halogen, carboxyl, cyano, nitro, ($C_1$-$C_6$)alkyl, ($C_1$-$C_6$)haloalkyl, ($C_1$-$C_4$)hydroxyalkyl, ($C_2$-$C_4$)alkoxyalkyl, ($C_2$-$C_4$)haloalkoxyalkyl, ($C_2$-$C_4$)alkenyl, ($C_2$-$C_4$)haloalkenyl, ($C_2$-$C_4$)alkynyl, ($C_3$-$C_4$)haloalkynyl, hydroxy, ($C_1$-$C_4$)alkoxy, ($C_1$-$C_4$)haloalkoxy, ($C_2$-$C_4$)alkenyloxy, ($C_2$-$C_4$)haloalkenyloxy, ($C_2$-$C_4$)alkynyloxy, ($C_3$-$C_4$)haloalkynyloxy, ($C_1$-$C_4$)alkylthio, ($C_1$-$C_4$)haloalkylthio, ($C_1$-$C_4$)alkylsulfinyl, ($C_1$-$C_4$)haloalkylsulfinyl, ($C_1$-$C_4$)alkylsulfonyl, ($C_1$-$C_4$)haloalkylsulfonyl, ($C_2$-$C_4$)alkenylthio, ($C_2$-$C_4$)haloalkenylthio, ($C_2$-$C_4$)alkenylsulfinyl, ($C_2$-$C_4$)haloalkenylsulfinyl, ($C_2$-$C_4$)alkenylsulfonyl, ($C_2$-$C_4$)haloalkenylsulfonyl, ($C_2$-$C_4$)alkynylthio, ($C_3$-$C_4$)haloalkynylthio, ($C_3$-$C_4$)alkynylsulfinyl, ($C_3$-$C_4$)haloalkynylsulfinyl, ($C_3$-$C_4$)alkynylsulfonyl, ($C_3$-$C_4$)haloalkynylsulfonyl, ($C_1$-$C_6$)alkylamino, ($C_2$-$C_8$)dialkylamino, ($C_2$-$C_6$)alkylcarbonyl, ($C_2$-$C_6$)alkoxycarbonyl, ($C_2$-$C_6$)alkylaminocarbonyl, ($C_3$-$C_8$)dialkylaminocarbonyl, ($C_3$-$C_6$)trialkylsilyl, phenyl, phenoxy or a 5- or 6-membered heteroaromatic ring, each phenyl ring, phenoxy ring or 5- or 6-membered heteroaromatic ring optionally substituted with 1-3 substituents independently of one another selected from $R^{28}$; or two adjacent radicals $R^x$ together form a group —$OCH_2O$—, —$CH_2CH_2O$—, —$OCH_2CH_2O$—, —$OCH(CH_3)O$—, —$OC(CH_3)_2O$—, —$OCF_2O$—, —$CF_2CF_2O$—, —$OCF_2CF_2O$— or —CH=CH—CH=CH—; or ($C_1$-$C_6$)-alkyl, optionally substituted with 1-3 radicals $R^y$, which, independently of one another, are halogen, ($C_2$-$C_6$)alkenyl, ($C_2$-$C_6$)haloalkenyl, ($C_1$-$C_3$)alkoxy, ($C_1$-$C_2$)haloalkoxy, ($C_1$-$C_3$)alkylthio, ($C_1$-$C_2$)haloalkylthio or optionally substituted aryl; or ($C_2$-$C_6$)-alkenyl, optionally substituted with 1-3 radicals $R^z$, which, independently of one another, are halogen, ($C_1$-$C_6$)alkyl, ($C_1$-$C_6$)haloalkyl, ($C_1$-$C_3$)alkoxy, ($C_1$-$C_2$)haloalkoxy, ($C_1$-$C_3$)alkylthio or ($C_1$-$C_2$)haloalkylthio;

$R^2$ is H, F, Cl, Br, I, CN, $NO_2$, $OR^5$, $SR^6$ or $N(R^7)R^8$; in which $R^5$ is H, ($C_1$-$C_4$)alkyl or ($C_1$-$C_3$)haloalkyl, $R^6$ is H, ($C_1$-$C_4$)alkyl or ($C_1$-$C_3$)haloalkyl and $R^7$ and $R^8$, independently of one another, are H or ($C_1$-$C_4$)alkyl; and $R^{28}$ is, in each case independently of the others, halogen, cyano, nitro, ($C_1$-$C_6$)alkyl, ($C_1$-$C_6$)haloalkyl, ($C_2$-$C_4$)alkenyl, ($C_2$-$C_4$)haloalkenyl, ($C_3$-$C_4$)alkynyl, ($C_3$-$C_4$)haloalkynyl, ($C_1$-$C_4$)alkoxy, ($C_1$-$C_4$)haloalkoxy, ($C_1$-$C_4$)alkylthio, ($C_1$-$C_4$)haloalkylthio, ($C_1$-$C_4$)alkylsulfinyl, ($C_1$-$C_4$)alkylsulfonyl, ($C_1$-$C_4$)alkylamino, ($C_2$-$C_8$)dialkylamino, ($C_2$-$C_4$)alkylcarbonyl, ($C_2$-$C_6$)alkoxycarbonyl, ($C_2$-$C_6$)alkylaminocarbonyl, ($C_3$-$C_8$)dialkylaminocarbonyl or ($C_3$-$C_6$)trialkylsilyl.

13. A compound of formula (I) or an N-oxide or an agrochemically suitable salt thereof as claimed in claim 1, in which the radicals have the following meaning.
- $R^1$ is 2-F-4-Cl-Phenyl,
- $R^2$ is Cl,
- $R^3$ is H, and
- $R^4$ is H.

14. A compound of formula (I) or N-oxide or agrochemically suitable salt thereof as claimed in claim 1, in which the radicals have the following meaning:
- $R^1$ is phenyl, optionally substituted with 1-3 radicals $R^x$, which, independently of one another, are halogen, carboxyl, cyano, nitro, $(C_1\text{-}C_6)$alkyl, $(C_1\text{-}C_6)$haloalkyl, $(C_1\text{-}C_4)$alkoxy, $(C_1\text{-}C_4)$haloalkoxy; or
  - $(C_1\text{-}C_6)$alkyl, optionally substituted with 1-3 radicals $R^y$, which, independently of one another, are halogen, $(C_1\text{-}C_3)$alkoxy or $(C_1\text{-}C_2)$haloalkoxy or unsubstituted phenyl or phenyl substituted by a halogen; or
  - $(C_2\text{-}C_6)$alkenyl, optionally substituted with 1-3 radicals $R^z$, which, independently of one another, are halogen, $(C_1\text{-}C_6)$alkyl, $(C_1\text{-}C_6)$haloalkyl, $(C_1\text{-}C_3)$alkoxy or $(C_1\text{-}C_2)$haloalkoxy;
- $R^2$ is F, Cl, Br, I, or $NO_2$;
- $R^3$ is H, $(C_1\text{-}C_4)$alkyl, $(C_2\text{-}C_4)$alkenyl, $C(=O)R^{12}$, in which $R^{12}$ is H, $(C_1\text{-}C_4)$alkyl, $(C_1\text{-}C_3)$haloalkyl, $(C_1\text{-}C_4)$alkoxy, or $OR^{13}$, in which $R^{13}$ is H, $(C_1\text{-}C_4)$alkyl or $(C_1\text{-}C_3)$haloalkyl; and
- $R^4$ is H or $(C_1\text{-}C_4)$alkyl.

15. A compound of formula (I) or N-oxide or agrochemically suitable salt thereof as claimed in claim 1, in which the radicals have the following meaning:
- $R^1$ is phenyl, optionally substituted with 1-3 radicals $R^x$, which, independently of one another, are halogen, carboxyl, nitro, $(C_1\text{-}C_6)$alkyl, $(C_1\text{-}C_6)$haloalkyl, $(C_1\text{-}C_4)$alkoxy; or
  - $(C_1\text{-}C_6)$alkyl, optionally substituted with 1-3 radicals $R^y$, which, independently of one another, are halogen, phenyl or 4-halophenyl;
- $R^2$ is F, Cl, Br, or $NO_2$;
- $R^3$ is H or $(C_1\text{-}C_4)$alkyl; and
- $R^4$ is H or $(C_1\text{-}C_4)$alkyl.

* * * * *